(12) United States Patent
Sahani et al.

(10) Patent No.: US 11,969,577 B1
(45) Date of Patent: Apr. 30, 2024

(54) WEARABLE DRUG DELIVERY DEVICE FOR DISEASE MANAGEMENT AND SYSTEM THEREFOR WITH ARTIFICIAL INTELLIGENCE

(71) Applicant: Hana Patent Technology, LLC, Peoria, AZ (US)

(72) Inventors: Mandeep Sahani, Mesa, AZ (US); An-Dien Nguyen, Fremont, CA (US); J. Allan Waitz, Gold Canyon, AZ (US); Linh C. Nguyen, Surprise, AZ (US)

( * ) Notice: Subject to any disclaimer, the term of this patent is extended or adjusted under 35 U.S.C. 154(b) by 541 days.

(21) Appl. No.: 17/147,112

(22) Filed: Jan. 12, 2021

Related U.S. Application Data

(60) Provisional application No. 62/960,754, filed on Jan. 14, 2020.

(51) Int. Cl.
| | |
|---|---|
| A61M 5/172 | (2006.01) |
| A61B 5/00 | (2006.01) |
| A61B 5/145 | (2006.01) |
| A61M 5/142 | (2006.01) |
| G16H 20/17 | (2018.01) |
| G16H 40/67 | (2018.01) |
| G16H 70/60 | (2018.01) |

(52) U.S. Cl.
CPC ........ *A61M 5/1723* (2013.01); *A61B 5/14535* (2013.01); *A61B 5/14546* (2013.01); *A61B 5/4839* (2013.01); *A61M 5/14248* (2013.01); *G16H 20/17* (2018.01); *G16H 40/67* (2018.01); *G16H 70/60* (2018.01); *A61M 2202/0433* (2013.01); *A61M 2205/3584* (2013.01); *A61M 2205/52* (2013.01); *A61M 2205/8206* (2013.01); *A61M 2230/20* (2013.01)

(58) Field of Classification Search
CPC ............ A61M 5/1723; A61M 5/14248; A61M 2202/0433; A61M 2205/3584; A61M 2205/52; A61M 2205/8206; A61M 2230/20; A61B 5/14535; A61B 5/14546; A61B 5/4839; G16H 20/17; G16H 40/67; G16H 70/60

See application file for complete search history.

(56) References Cited

U.S. PATENT DOCUMENTS

| | | | |
|---|---|---|---|
| 10,303,851 B2 | 5/2019 | Nguyen et al. | |
| 2014/0276552 A1* | 9/2014 | Nguyen, Jr. | ........ A61M 5/1723 705/2 |
| 2015/0220700 A1* | 8/2015 | Chait | ................. A61K 38/1816 702/19 |

* cited by examiner

*Primary Examiner* — Scott J Medway
(74) *Attorney, Agent, or Firm* — Eugene Vamos

(57) ABSTRACT

Apparatus(es)/method(s) relating generally to remotely administering a medication is/are disclosed. In one such method, a drug delivery device is obtained. The drug delivery device has: at least one reservoir in fluid communication with a needle; at least one actuator to drive a fluid within a respective at least one reservoir to the needle; a microcontroller to control operation of the at least one actuator; and a dosage control loop configured for communication with the microcontroller and a hemoglobin sensor. A dosage provided by the drug delivery device is automatically adjusted responsive to hemoglobin count sensed by the hemoglobin sensor for transdermal administration of medication for management of chronic kidney disease.

8 Claims, 18 Drawing Sheets

WEARABLE DRUG DELIVERY DEVICE FOR DISEASE MANAGEMENT AND SYSTEM THEREFOR WITH ARTIFICIAL INTELLIGENCE

CROSS-REFERENCE TO RELATED APPLICATIONS

The present application claims the benefit of priority to U.S. Provisional Patent Application No. 62/960,754, filed Jan. 14, 2020, which is hereby incorporated by reference in its entirety for all purposes to the extent same is consistent herewith.

TECHNICAL FIELD

The following description relates to health care. More particularly, the following description relates to a wearable drug delivery device for disease management. Even more particularly, the following description relates to a wearable drug delivery device for kidney disease management and a system therefor with artificial intelligence.

BACKGROUND

Health care delivery is complicated and costly. Caring for patients in remote areas, such as for example rural areas, can make such complications and/or costs more severe. Additionally, a medical professional's time is a limited resource and can be costly.

SUMMARY

A system relates generally to disease management. In such a system, there is a drug delivery device. The drug delivery device has: at least one reservoir in fluid communication with a needle; at least one actuator to drive a fluid within a respective at least one reservoir to the needle; a microcontroller to control operation of the at least one actuator; and a dosage control loop configured for communication with the microcontroller and a hemoglobin sensor. The drug delivery device is configured for automated adjustment of dosage responsive to hemoglobin count sensed by the hemoglobin sensor for transdermal administration of medication for management of chronic kidney disease.

A method relates generally to remotely administering a medication. In such a method, a drug delivery device is obtained. The drug delivery device has: at least one reservoir in fluid communication with a needle; at least one actuator to drive a fluid within a respective at least one reservoir to the needle; a microcontroller to control operation of the at least one actuator; and a dosage control loop configured for communication with the microcontroller and a hemoglobin sensor. A dosage provided by the drug delivery device is automatically adjusted responsive to hemoglobin count sensed by the hemoglobin sensor for transdermal administration of medication for management of chronic kidney disease.

Other features will be recognized from consideration of the Detailed Description and Claims, which follow.

BRIEF DESCRIPTION OF THE DRAWINGS

Accompanying drawings show exemplary apparatus(es) and/or method(s). However, the accompanying drawings should not be taken to limit the scope of the claims, but are for explanation and understanding only.

FIG. 15-1 is a flow diagram depicting an example of a CKD management flow for CKD stages 1 and 2.

FIG. 15-2 is a flow diagram depicting an example of a CKD management flow for a CKD stage 3A.

FIG. 15-3 is a flow diagram depicting an example of a CKD management flow for a CKD stage.

FIG. 15-4 is a flow diagram depicting an example of a CKD management flow for CKD stages 4 and 5.

DETAILED DESCRIPTION

Figure 1:
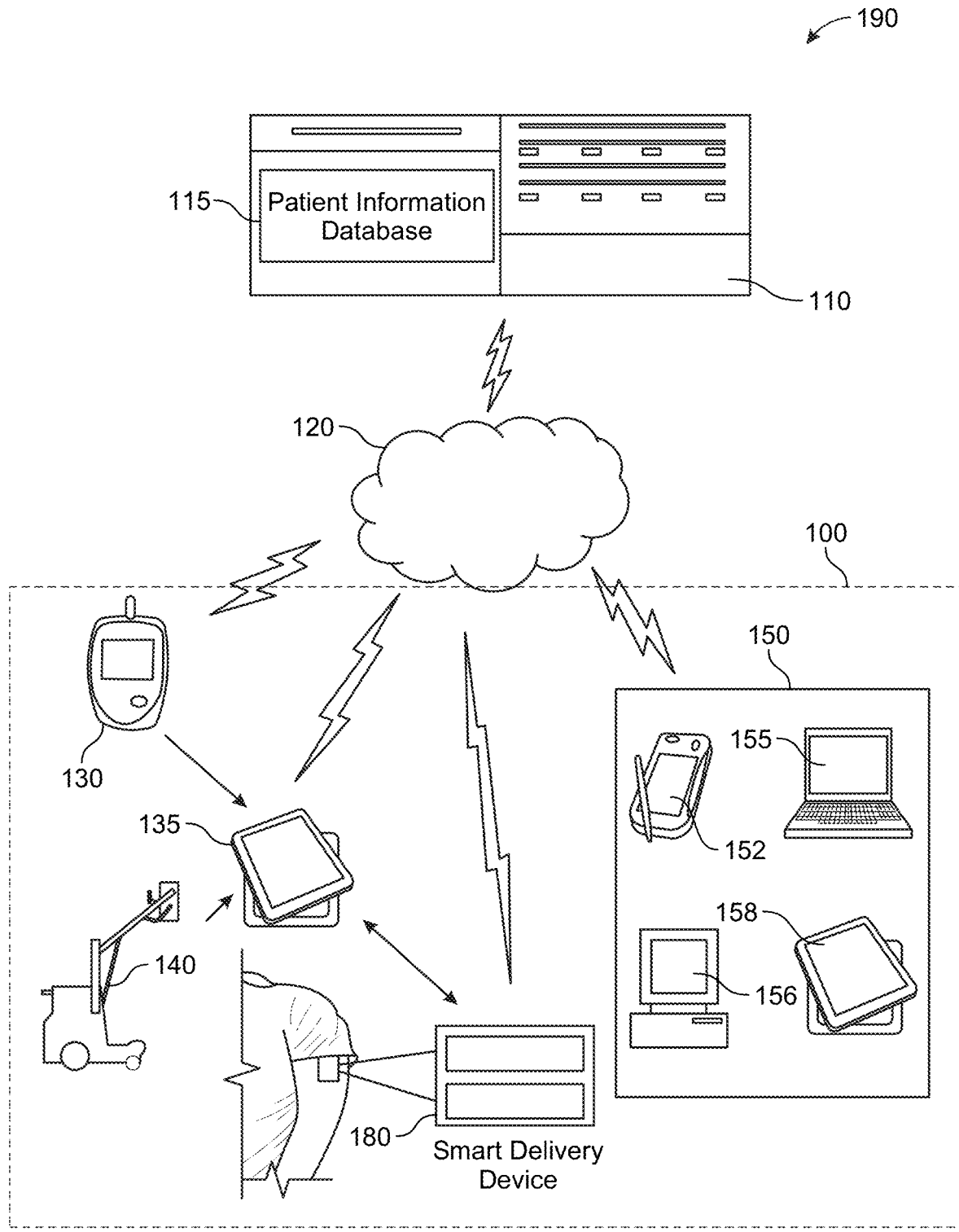
FIG. 1 is a general schematic diagram depicting an example of a physician-centric health care delivery system ("PCH care delivery system").

In the following description, numerous specific details are set forth to provide a more thorough description of the specific examples described herein. It should be apparent, however, to one skilled in the art, that one or more other examples and/or variations of these examples may be practiced without all the specific details given below. In other instances, well known features have not been described in detail so as not to obscure the description of the examples herein. For ease of illustration, the same number labels are used in different diagrams to refer to the same items; however, in alternative examples the items may be different.

Exemplary apparatus(es) and/or method(s) are described herein. It should be understood that the word "exemplary" is used herein to mean "serving as an example, instance, or illustration." Any example or feature described herein as "exemplary" is not necessarily to be construed as preferred or advantageous over other examples or features.

Reference will now be made in detail to examples which are illustrated in the accompanying drawings. In the following detailed description, numerous specific details are set forth in order to provide a thorough understanding of the following described implementation examples. It should be apparent, however, to one skilled in the art, that the implementation examples described below, including one or more aspects thereof, may be practiced without all the specific details given below. Moreover, the example implementations are not intended to be exhaustive or to limit scope of this disclosure to the precise forms disclosed, and modifications and variations are possible in light of the following teachings or may be acquired from practicing one or more of the teachings hereof. The implementation examples were chosen and described in order to clearly explain principles and practical applications of the teachings hereof to enable others of ordinary skill in the art to utilize one or more of such teachings in various implementation examples and with various modifications as are suited to the particular use contemplated. In other instances, well-known methods, procedures, components, circuits, and/or networks have not been described in detail so as not to unnecessarily obscure the described implementation examples.

For purposes of explanation, specific nomenclature is set forth to provide a thorough understanding of the various concepts disclosed herein. However, the terminology used herein is for the purpose of describing particular examples only and is not intended to be limiting. As used herein, the singular forms "a", "an" and "the" are intended to include the plural forms as well, unless the context clearly indicates otherwise. As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context. It will also be understood that the term "and/or" as used herein refers to and encompasses any and all possible combinations of one or more of the associated listed items. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof. It will also be understood that, although the terms first, second, etc. may be used herein to describe various elements, these elements should not be limited by these terms, as these terms are only used to distinguish one element from another.

Some portions of the detailed descriptions that follow may be presented in terms of algorithms and symbolic representations of operations on data bits, including within a register or a memory. These algorithmic descriptions and representations are the means used by those skilled in the data processing and other computer and/or information science arts to most effectively convey the substance of their work to others skilled in the art. A process flow as herein is generally conceived to be a self-consistent sequence of steps leading to a desired result. The steps may be those involving physical manipulations of physical quantities. Usually, though not necessarily, these quantities take the form of optical, electrical or magnetic signals capable of being stored, transferred, combined, compared, and otherwise manipulated. For convenience at times, principally for reasons of common usage, reference is made to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to action(s) and/or process(es) of a computer system, or similar electronic computing device, that manipulates and transforms data represented as physical (electronic) quantities within the computer system's registers or memories into other data similarly represented as physical quantities within the computer system memories or registers or other such information storage, transmission or display devices thereof and/or associated therewith.

Concepts described herein may be embodied as apparatus, method, system, or computer program product. Accordingly, one or more of such implementation examples may take the form of an entirely hardware implementation example, an entirely software implementation example (including firmware, resident software, and micro-code, among others) or an implementation example combining software and hardware, and for clarity any and all of these implementation examples may generally be referred to herein as a "circuit," "module," "system," "block" or other suitable terms. Furthermore, such implementation examples may be of the form of a computer program product on a computer-usable storage medium having computer-usable program code in such medium.

Any suitable computer usable or readable medium may be utilized. A computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory ("RAM"), a read-only memory ("ROM"), an erasable programmable read-only memory ("EPROM" or Flash memory), an optical fiber, a portable compact disc read-only memory ("CD-ROM"), an optical storage device, a transmission media such as those supporting the Internet or an intranet, or a magnetic storage device. The computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, radio frequency ("RF") or other means. For purposes of clarity by way of example and not limitation, the latter types of media are generally referred to as transitory signal bearing media, and the former types of media are generally referred to as non-transitory signal bearing media.

Computer program code for carrying out operations in accordance with concepts described herein may be written in an object oriented programming and/or scripting language, which may include one or more of Java, Python, Smalltalk, C++ or the like. Program code for carrying out such operations may be written in conventional procedural languages whether directly machine readable or involving compiling or interpreting. The program code may execute entirely on the user's computer, partly on the user's computer, as a stand-alone software package, partly on the user's computer and partly on a remote computer or entirely on the remote computer or server or cloud-based infrastructure. In the latter scenario, the remote computer may be connected to the user's computer through a wired or wireless local area network ("LAN") or a wide area network ("WAN"), or the connection may be made to an external computer (for example, through the Internet using an Internet Service Provider).

Systems and methods described herein may relate to an apparatus for performing the operations associated therewith. This apparatus may be specially constructed for the purposes identified, or it may include a general-purpose computer selectively activated or reconfigured by a computer program stored in the computer.

Notwithstanding, the algorithms and displays presented herein are not inherently related to any particular computer or other apparatus. Various general-purpose systems may be used with programs in accordance with the teachings herein, or it may prove convenient to construct a more specialized apparatus to perform the operations. In addition, even if the following description is with reference to a programming language, it should be appreciated that any of a variety of programming languages may be used to implement the teachings as described herein.

One or more examples are described below with reference to flowchart illustrations and/or block diagrams of methods, apparatus (including systems) and computer program products. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the Figures illustrate the architecture, functionality, and operation of possible implementations of apparatuses (including systems), methods and computer program products according to various implementation examples. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

It should be understood that although the flow charts provided herein show a specific order of operations, the order of these operations may differ from what is depicted. Also, two or more operations may be performed concurrently or with partial concurrence. Such variation will depend on the software and hardware systems chosen and on designer choice. It is understood that all such variations are within the scope of the disclosure. Likewise, software and web implementations may be accomplished with standard programming techniques with rule based logic and other logic to accomplish the various database searching operations, correlation operations, comparison operations and decision operations. It should also be understood that the word "component" as used herein is intended to encompass implementations using one or more lines of software code, and/or hardware implementations, and/or equipment for receiving manual inputs.

Before describing the examples illustratively depicted in the several figures, a general introduction is provided to further understanding.

A nurse-centric health care delivery system for remote telehealth/telemedicine monitoring ("RTM") has been used to address health care for limited mobility and/or remotely located patients, such as elderly and/or rural patients. In the past, these efforts failed to show significant reduction in hospital readmissions, emergency room ("ER") admissions, and/or overall healthcare costs.

A physician-centric health care delivery system used in conjunction with RTM can be more effective in reducing ER and hospital admissions/readmissions. Such a physician-centric health care delivery system may be made even more cost effective and result in better care if used in conjunction with in a home care and/or nursing home care setting.

Such a physician-centric health care delivery system may incorporate a physician-based clinical decision support system ("PCDSS") integrated with an RTM platform. Such an integrated system may analyze data and diagnose a medical condition of a patient. Such an integrated system may further administer health care to a patient in real-time. This real-time health care treatment may additionally include providing a treating physician with one or more recommended treatment options.

A physician-centric health care delivery system may include a "smart" delivery device capable of automatically administering medications to a wearer of such a delivery device. A "smart" delivery device may further be adapted to communicate remotely, such as with a physician, such as to modify the amount or type of drug being delivered. By having a "smart" delivery device a patient wearable or wearable device, a patient may wear such device throughout a day, including without limitation during routine daily activities. Along those lines, one or more integrated wearable devices, such as an iHealth, Fitbit, and/or Misfit integrated with a "smart" delivery device as described herein and used with a telemedicine platform, such as described herein, may be used to provide a patient with a remote telehealth/telemedicine device to generate real-time patient health information. Such real-time patient health information may include one or more of weight, blood pressure, and pulse oxygenation. Such information may further include medication changes and/or lab results immediately upon electronic availability.

While a physician-centric health care delivery system as described herein may be used to address health care of non-hospitalized patients, such a physician-centric health care delivery system may be used to address health care of hospitalized patients. As hospitals may be campuses with significant distances between buildings, a remote monitoring system of a physician-centric health care delivery system may be used to allow for distributed monitoring.

A physician-centric health care delivery system may be used in conjunction with personal care visits by a medical professional, which may be performed as determined, to further reduce readmissions and thus health care costs. However, such visits may be used to collect data for continued monitoring. Furthermore, while on-premises personal care visits may be used, virtual contacts with a patient may be used for such personal care visits, namely virtual visits. Along those lines, a physician-centric health care delivery system as described herein may be used with video conferencing, augmented reality, virtual reality, audio conferencing, and/or other virtual contact systems.

Data collection for electronic health record ("EHR") databases may be from various sources for a patient's health care. A physician-centric health care delivery system as described herein may be used with one or more EHR databases.

More recently, artificial intelligence ("AI"), including machine learning, has been used for health care. Along those lines, AI computing can be used for predicting, such as using three-dimensional (3D) image processing, of physical conditions. This information may be useful for developing diagnosis and treatment, among other applications. More broadly, AI may be used to obtain understanding of meaning from collected data.

However, because AI often seeks to determine patterns in an existing data set, studies have found such AI results to be inaccurate when another bigger data set is processed. Accordingly, reproducibility can be a significant limitation in ensuring correct diagnosis and treatment using machine learning techniques.

A physician-centric health care delivery system for diagnosing and/or treating a patient may include at least one database accessible via a server for storing and retrieving related patient and other health data. Such health data may include one or more of real-time patient health data, a clinical practice guideline, answers to a patient questionnaire, and/or a patient medical history. Such a server may be operative to access such database responsive to health care diagnosis and possible treatment responsive to such diagnosis. A computing device remotely located from such a server, including a programmed general-purpose microprocessor or one or more processor cores, which when programmed provide a "special-purpose processor," and memory, may be configured to store and execute one or more components, including an interface, of a diagnostic application for communication with such a server for retrieving of health data for execution of such diagnostic application. Such a diagnostic application may generate at least one patient diagnosis and may provide a patient treatment recommendation for such at least one patient diagnosis. One or more possible diagnoses and one or more possible treatments may be generated, at least in part, using AI. However, because such AI results may be inconsistent due to data set or other limitations, such possible diagnoses and treatments may be reviewed by a medical professional prior to informing a patient and/or performing treatment on a patient in a physician-centric health care delivery system.

With the above general understanding borne in mind, various configurations of physician-centric health care delivery systems and related processes are generally described below.

For purposes of clarity by way of non-limiting example, physician-centric health care delivery systems and processes are described to address health care of non-hospitalized patients, such as for example patients living at home, in an assisted living facility, or in a nursing care facility. However, such a physician-centric health care delivery systems and processes may be used for hospitalized patients.

For purposes of clarity by way of non-limiting example, physician-centric health care delivery systems and processes are described as implemented in a combination of hardware and software via a networked system. However, other implementations, whether limited more to hardware or software, may be used. Additionally, for purposes of clarity by way of non-limiting example, physician-centric health care delivery systems and processes are described as implemented using both wireless and wired networking; however, either or both wireless and wired networking may be used in other implementations.

More particularly, for purposes of clarity by way of non-limiting example, a physician-centric health care delivery system and process directed to health care of patients, particularly elderly or others with limited or no ambulatory ability, is described for telemedicine and other medical care delivery systems. Even though an example of personal care visits by a medical professional to a patient to a regional, mobile or other designated care giving facility may be used to reduce readmissions and health care costs, in another example a patient may be equipped with a programmable drug delivery device to deliver medications. Such delivery of medications may be responsive to a schedule and/or interdiction responsive to one or more medical conditions. Such interdiction may be for an emergent condition, which may be detected and responded to by an artificial intelligence engine.

Accordingly, because of the multifariousness of health care, specific examples, such as for a kidney condition, are provided for purposes of clarity and not limitation. Along those lines, these or other examples for delivery of health care with a physician-centric health care delivery system or related process may be used.

FIG. 1 is a general schematic diagram depicting an example of a physician-centric health care delivery system ("PCH care delivery system") 190 having a PCDSS 100. PCH care delivery system 190 is described as using network access via the Internet; however, other networking configurations may be used in accordance with the following description.

PCH care delivery system 190 includes a server 110 in communication with a network 120, which may include via the Internet 120. However, for patient privacy rights it should be appreciated that connections herein are secured, such as with virtual private networking, private networking, point-to-point encrypting, and/or other privacy protection technology. In the event of an emergency, PCH care delivery system 190, which may be subject to obtaining a patient's consent in advance, may go out or be taken out of private communication in favor of public communication to address an exigent circumstance where a private communication system is not presently working or working too slowly for an emergency condition. Along those lines, for a PCH care delivery system 190, a user may purchase a more reliable and/or higher bandwidth from an Internet Service Provider.

Server 110 may be operative to access a patient information database 115. In this example, a patient information database 115 is stored locally in or nearby server 110 to reduce potential for unlawful exposure of patient data. Accordingly, a dedicated hardwired point-to-point connection to enhance security for privacy reasons. Along those lines, to further protect patient privacy, a diagnostic application may be "moved" to patient information database 115 for accessing and processing data therein rather than moving such data to such diagnostic application.

Having at least one computing device remotely located from server 110, where such computing device includes a microprocessor configured to execute a physician-centric clinical support system application, namely a diagnostic computer application or diagnostic application. Such computing device may be configured for continuous communication with server 110. A Health Information Exchange ("HIE") module may be configured to continuously process new records coming from a communication/connection layer to support multiple data transmission protocols, such as for example: http, ftp, or webDav, among others, as well as various data formats (e.g., JSON, XML for HL7 v3, or plain text, among others) of such communicated data from an Health Information Exchange system ("HIE system"), such as for example, AZHEC (Arizona Health E-Connect) which is funded by state and federal grants.

This transmission may be through a Mirth Sftp connection under HL7 or other transmission protocol to provide compliance with many HIE platforms. A Restful API or other API may be used to allow retrieving and manipulating data from another platform (e.g., Back Office Xystem ("BOX"), AdvanceMD, or other third party platform), and then filtering active patients and abnormal lab tests to generate a list of high risk patients for screening. This list can be access from inside a BOX or other back office system subject to restricted access. For example, such a restriction may be to only "incharge" a person where there is a need to log access and operations for auditing (e.g., HIPAA compliance). A third party platform may further include a data warehouse for querying big sets of data, such as for statistical computations, predictive analytics, or other big data analysis, such as under Apache Hadoop or other big data organization framework.

A diagnostic application may include an algorithm with logic designs for population health, such as kidney failure, which population may be delineated based on age, weight, blood pressure, lab results, risk scores, demographics, and/or other criteria to decide whether a patient should be medically taken care by a clinician healthcare in-person at home, via telemedicine, with medications delivery by drones home, or with admittance into a contracted skilled nursing facility instead of a hospital.

An integrated dialysis delivery system through epoetin alfa smart diagnostic and medication smart patch as described herein may automatically trigger and create a medical chart, among other items as described herein. A telemonitoring system and method for diagnosing and/or treating a patient may include a patient information database for storing and retrieving patient health data, including associated medical history. Such medical history may include a renal diagnosis, which can help establish a sound basis for a mediated medical intervention through a telemedicine support team of a Physician-Clinical Decision Support System (PCDSS). As described below in additional detail, such a PCDSS may be configured with pre-programmed Artificial Intelligence (AI) algorithms. One or more of such AI algorithms may efficiently provide proper medical guidance and treatment to remotely situated patients. A platform of a Physician-Centric Healthcare Delivery System (PCHDS) provides a convenient approach to improve communication between physicians and patients for the early detection of renal failure. Along those lines, an anemia diagnosis may have detected through hemoglobin count a renal failure leading to treatment through an administration of Epogen or Erythropoietin hormone. This hormonal treatment be performed by patients on themselves, in some instances single-handedly, using smart diagnostic and medication patch, as described below in additional detail. An available care team member may coordinate with a patient for such treatment. Along those lines, such a system may deploy and send a SMS, email, or other electronic message to such patient in regard to a treatment plan. Depending on patients' choice, each patient can choose to have an "in-person" physical exam at home which may include an Uber-like house call visit or a telemedicine remote physical exam with an iHealth Kit or like health kit having smart device as described herein synchronized and in communication with such health kit. Once a telemedicine remote physical exam is completed, medications and/or Durable Medical Equipment ("DME") can be delivered to such patient's address, such as by drone, self-driving vehicle, or other means.

Automated care decisions and delivery support systems under control of a diagnostic computer application, though subject to a patient's previously input care desires, may be processed in real time such as at a state HIE's server to deliver health care to a patient in a timely and accurate manner at less cost. Along those lines, because a system as described herein with automated processing can coordinate for example with a minimum of 150 patients at the same time, patient care may be provided with substantially fewer mishaps and with a reduction in overall medical professional time. Moreover, such care may tie into Six Sigma tools and techniques for quality assurance to monitor such process at different times.

Patient information database 115 may be for storing and retrieving data related to a patient and may include real-time patient health information, one or more clinical practice guidelines and patient medical history/questionnaire responses. To populate patient information database 115 with patient data, as well as to monitor and treat patients, each patient (for example a patient indicating kidney failure) may receive an RTM device 130.

RTM device 130 may be configured to allow a patient to take their vital signs and/or other medical data. These vital signs and/or other medical data to be monitored may be informed by a physician's direction, order, prescription, and/or other instruction. Such RTM device 130 may be used in the comfort of a patient's home or residence, including in a nursing care or assisted living facility.

Patient vital sign data may be entered manually by a patient or may be measured and recorded automatically by RTM device 130. RTM device 130 may be configured for wireless communication with server 110 via network 120. Patient health data, such as measured by or with RTM device 130, may be wirelessly communicated directly to network 120 for server 110, or patient health data, such as measured by or with RTM device 130, may be loaded onto or wirelessly communicated to a local computing device 135 for uploading to server 110 via network 120. Patient health information may include real-time patient health data, as well as other data such as labs, medication, radiology, and/or diagnosis data.

Examples of computing device 135 may include a smart phone, a laptop or notebook computer, a personal or desktop computer, a tablet such as an iPad, a smart phone such as an iPhone, or other computing device. Computing device 135 may be configured to provide a data hub service with temporary local storage of patient medical data. Such patient medical data may be encrypted temporarily stored and communicated in an encrypted form for patient privacy.

Computing device 135 may be configured patients to complete online questionnaires regarding their health, as well as allowing patients to view their medical chart/history. Computing device 135 may further be configured for communication between patients and physicians through use of electronic mail and/or video conferencing, such as Skype, FaceTime, Zoom, WebEx, Vring, and the like.

In an example, a patient may be fitted with a "smart" delivery device 180. Delivery device 180 may be configured to mechanically or automatically, which may be responsive to instruction, dispense medication to a patient, as described below in additional detail. Smart delivery device 180 may be configured for wireless communication with computing device 135 for communication over network 120.

A physician-centric health care delivery system platform may include a web-based application. This web-based application may allow physicians access anywhere through a wired or wireless connection, such as over the Internet or by using a 4G or later generation configured mobile device, like an iPhone, iPad, Android-based pad, or Android-based phone for example; a mobile device may include a tablet computing device 125.

By utilizing a web-based system, a treating physician can use a PCDSS application to access patient information database 115, such as via server 110, from for example any Internet accessible location using a programmed computing device 150, such as with a web browser. Along those lines, such a PCDSS may include Cloud-based components. Examples of suitable computing devices for computing device 150 include a smart device, such as smart phone/PDA/iPhone 152, laptop computer 155, personal computer (PC) 156, and tablet PC or iPad 158.

A PCDSS application may assist physicians in providing an accurate diagnosis of a patient's medical condition based on patient data from patient information database 115. Such patient data may include a patient's EHR, a Patient Health Record ("PHR"), periodic, such as for example current daily, data from one or more RTM devices 130, and patient questionnaires/medical history responses. Relevant patient data from patient information database 115 may include patient history, previous encounter history, drug allergies, age, weight, and sex, among other possible factors. Such patient data may be input to a PCDSS analytical engine to suggest appropriate diagnostic and treatment options. Physicians can review and modify such suggested diagnostic and treatment options to recommend a course of health care. Again, such diagnostic and treatment options may be limited by a data set used to generate same, and as such data set may impose unforeseen limitations, which when output of such PCDSS analytical engine is reviewed by a physician may be apparent so as to avoid an erroneous diagnosis and/or treatment.

In an example, an integrated in-home capable dialysis delivery system through epoetin alfa-based treatment delivered through a smart diagnostic and medication patch is described below in additional detail. Such a drug delivery system may include a smart medication patch for monitoring and diagnosing anemia and delivering liquid medication to treat anemia. A common complication brought about by chronic kidney disease (CKD) is associated with delivery of liquid medication to treat anemia. In the example of a system with smart medical patch drug delivery in conjunction with a remote telemonitoring capability of a PCHDS alongside PCDSS, a telemedicine clinician support team, combined with AI algorithms, may provide diagnostic and medication orders to patients, which may be useful particularly in remote and rural areas.

CKD, also called chronic kidney failure, describes a gradual loss of kidney function, such as an inability of one or more kidneys, generally both kidneys, to filter wastes and excess fluids from a person's blood. This inability to filter may mean such unfiltered contents are subsequently excreted in a person's urine. One way to do this is with a urine test to assess a patient's albumin-creatinine ratio (ACR). An ACR ratio can indicate whether a protein is leaking into the urine (proteinuria), which is a sign of kidney damage. CKD is considered as a worldwide health crisis with tens of millions of deaths resulting therefrom.

There are generally five stages of CKD. During the early stages of CKD, signs or symptoms may not become apparent to or upon a patient until their kidneys' function is more significantly impaired. A blood test may be used to measure creatinine, urea, and other waste products in a patient's blood to determine whether kidneys are working within normal limits. Normal limits are based on an estimated glomerular filtration rate (eGFR). A GFR of greater than 90 m L/min is generally considered normal or high functioning. An accepted formula to calculate GFR includes body size, age, sex, and ethnicity. Eventually when CKD reaches an advanced stage, dangerous levels of fluid, electrolytes and wastes can build up in a person's body, which can result in various health complications, such as heart disease, bone disease, and/or anemia.

Anemia commonly occurs in people with CKD as it might begin to develop in the early stages of such disease when someone has 20 to 50 percent of normal kidney function. Anemia tends to worsen as CKD progresses, and most people who have total loss of kidney function, namely kidney failure, have anemia as a result.

In the US, treatment of chronic kidney disease is in the tens of billions of dollars per year. Treatment for kidney failure consumes over 6% of the total Medicare budget to care for less than 1% of the covered population. But with early diagnosis and treatment, CKD can be treated, as it is likewise possible to slow or stop the progression of kidney disease.

When the kidneys are diseased or damaged, they do not make enough Erythropoietin or EPO hormone (EPO). EPO is a hormone produced by a kidney. For diseased or damaged kidneys, bone marrow makes fewer red blood cells, resulting in a cell membrane fluctuation that engenders anemia. Epogen, in this example, is a medication given for treatment in people with long-term serious kidney disease and is usually administered through injection intravenously or subcutaneously for patients who may or may not be on dialysis.

Epogen is a man-made form of the protein human erythropoietin that is given to reduce or avoid a need for red blood cell transfusions. Epogen stimulates a person's bone marrow to make more red blood cells. Having more red blood cells raises hemoglobin level. If a hemoglobin level stays too high, or if a hemoglobin goes up too quickly, this may lead to serious health problems which may result in death. These serious health problems may happen even if a patient is on Epogen and does not have an increase in their hemoglobin level.

The introduction of Epogen in clinical practice, more than two decades ago, altered completely the management of patients with CKD. The successful correction of the anemia of CKD has resulted in reduction of associated morbidity and improvement of functionality, exercise tolerance, cognitive function and overall quality of life. Recently, large randomized clinical studies suggested that administration of Epogen targeting at complete anemia correction is accompanied by significant increase of morbidity and mortality, compared to partial anemia correction. This observation has led to a thorough investigation of the mechanisms of Epogen actions, and the possible contribution of other parameters including iron availability, comorbidities and resistance or hyporesponsiveness to Epogen. In this context, it has been proposed that high doses of Epogen are likely to exert toxic effects and pleiotropic systemic actions.

The consequences of renal anemia are mainly cardiovascular; left ventricular hypertrophy is often found at the start of dialytic therapy. Optimization of erythropoietin therapy includes awareness of target hematocrit and hemoglobin, defining the renal anemia management period, drug dosage and mode of application and significance of adjuvant therapy. It is recommended that anemia be treated early during the course of renal failure, even when glomerular filtration rate falls below 50 ml/min. According to Dialysis Outcomes Quality Initiative guidelines, target values are 0.33-0.36 L/L for hematocrit and 110-130 g/l for hemoglobin. Early administration is recommended especially in high-risk patients: the elderly, diabetics and those with coronary artery and peripheral artery diseases. EPO-therapy is well established and efficient for renal anemia in dialysis and pre-dialysis patients.

Hemodialysis patients were studied to determine whether a dose of recombinant human erythropoietin required to maintain a therapeutic hematocrit level changed when the route of administration was switched from intravenously (IV) three times per week to subcutaneously (SC) three times per week. The maintenance dose for patients who received Epoetin alfa diluted 1:2 with bacteriostatic saline (n=23) did not differ from the undiluted three times per week dose at the end of stage 1. The third cohort of patients (n=24), who continued to receive undiluted Epoetin alfa on the same SC three-times-per-week schedule, did not require a significant change in dosage over the ensuing 12 weeks. Comparison of SC three times per week mean dosage after an average of 32 weeks following the switch from IV three times per week for this latter cohort revealed a decrease of 23.5%+/−6.5% (P<0.001).

While subcutaneous drug administration is an accepted mode of delivering a liquid medication to hemodialysis patients, given the significant decrease of the erythropoietin dosage upon patients over those who were assigned to receive intravenous administration following a period of medication compliance. As described below in additional detail, transdermal delivery via micro-needles may be used for treatment and management.

Transdermal delivery of drugs is known, including an iontophoresis apparatus for applying local anesthetics. Transdermal delivery via microneedles is increasingly gaining traction as one of the more promising drug delivery technologies. Microneedles are of a few hundred microns in size, capable of creating transient pores across the skin by penetrating the stratum corneum layer to deliver molecules. These needles are not big enough to reach the nerve-rich regions of the skin; as a result, the drug delivery is perceived as completely painless and devoid of bleeding. Drugs, vaccines, proteins, peptides and other biomolecules are suitable for delivery using the microneedle technology.

In membrane transdermal patch systems, the active substance is dissolved or dispersed in a liquid or gel reservoir. On the outside, the reservoir is protected by a foil, while the other side is in contact with a membrane which controls the release of the active substance. An adhesive treated surface adheres a patch to skin and allows transport of an active substance. The release of such an active substance is controlled by a diffusion rate through such a membrane. However, membrane controlled diffusion can initially produce unintentionally rapid release because some of such active substance diffuses into such membrane and adhesive treated surface before use. Thus, the active substance in the adhesive surface is released before diffusion through the membrane determines the release rate.

In less conventional transdermal patches, an active substance is generally either dissolved or dispersed in a matrix. The outside of such matrix is covered with a protective layer, while there is an adhesive surface on the inside of such matrix. The release of an active substance from such matrix systems generally does not follow linear kinetics, rather release is faster than the absorption rate into human skin, and such skin may provide a linear absorption. Many attempts have been made to improve drug form by using passive methodologies that provide faster release rates. This involves, for example, the use of substances that improve penetration, prodrugs and super-saturated systems, and, to further increase the release, other methods such as iontophoresis, electroporation, ultrasound, microneedles or high temperature have been used. Transdermal patch strategy has been found to be effective in improving pharmacological compliance or adherence than in patients using capsules or tablets, leading to an increase of treatment benefits in patients with mental health problems such as Alzheimer's disease. Notably, for patients undergoing dialysis treatment with stage 4 or 5 of CKD, around 30% of those patients have serious mental health.

In a more recent development, a noninvasive, continuous hemoglobin monitoring, in which uses a portable hand-held device, provides real-time visibility to changes to hemoglobin between invasive blood samples. Moreover, an evaluation of noninvasive blood screening of hemoglobin using smartphone cameras was conducted through a "HemaApp" on 31 patients ranging from 6-77 years of age, yielding a 0.82 rank order correlation with the gold standard blood test. In screening for anemia, a HemaApp achieve a sensitivity and precision of 85.7% and 76.5%. Both regression and classification performances compare favorably using this noninvasive hemoglobin measurement device. Neither of the screening methodologies mentioned above was integrated into or with a smart medication drug delivery system in order that a comprehensive system of monitoring, diagnosis and treatment to patients may be provided to CKD patients with anemia. As described below in additional detail, wearable smart medication drug delivery and diagnostic patch may be used to address one or more of these issues. Along those lines, anemia management in a CKD setting may be addressed for blood monitoring efficiency and drug delivery to further medication compliance upon patients through the use of a smart monitoring and drug delivery medication device. As described below in additional detail, a smart medication drug delivery system for electronic health monitoring, diagnostic, and treatment administration is configured to help a physician-support team detect hemoglobin count and calculate accurate Epogen medication dosing and/or prescription to patients under home dialysis treatment, toward ensuring proper CKD and co-morbidities management.

With continuing reference to FIG. 1, if indicated by a patient's condition as monitored via RTM device 130, mobile medical support professionals, such as for example a home health nurse, a nurse practitioner, an emergency medical technician, or the like, may conduct additional medical tests using mobile medical device 140 at a patient's location, such as a patient's home, nursing care facility, assisted living facility, or other suitable location, such as for example, a medical clinic or a satellite/mobile facility such as an office building, a room in an office or a kiosk, without requiring the patient to be taken to, and possibly being admitted into, a hospital. Examples of additional medical tests may include a portable x-ray, ultrasound, mobile echocardiography, and on-site blood assays and analyses.

As with RTM device 130, mobile medical device 140 may be configured for wireless communication with server 110. Data generated by mobile medical device 140 may be loaded onto a computing device 135 for uploading to server 110 via network 120. Patient health information communicated to server 110 may be stored within a patient's designated individual PHR within patient information database 115. Optionally, a notice may be automatically sent, such as by push notice, text, and/or email for example, to a physician or other medical professional informing same that additional medical information is available for review within patient information database 115 once that information is loaded onto or through server 110. Further, as is discussed in greater detail below with regard to FIG. 2, a PCDSS may incorporate additional information to produce one or more updated diagnoses and/or treatment options for review by a physician.

Figure 2:
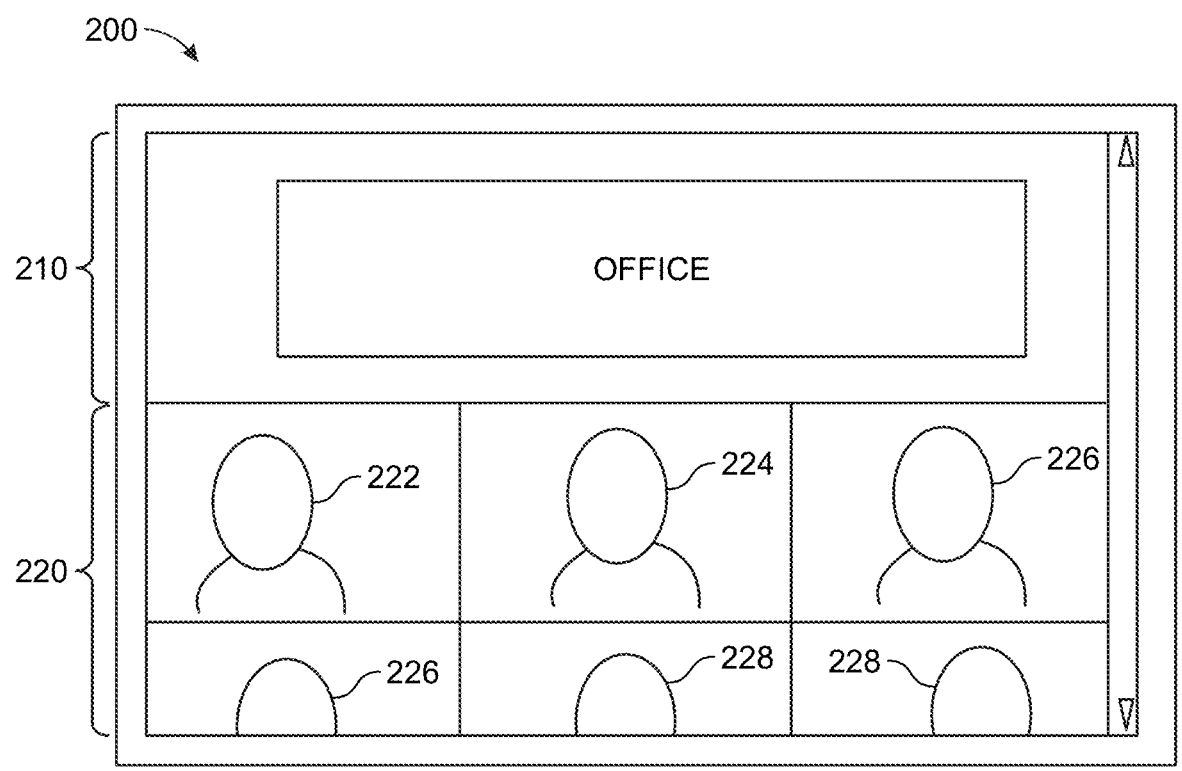
FIGS. 2 through 4 are respective generalized schematic diagrams of examples of screen displays using a videoconferencing software application.
Figure 3:
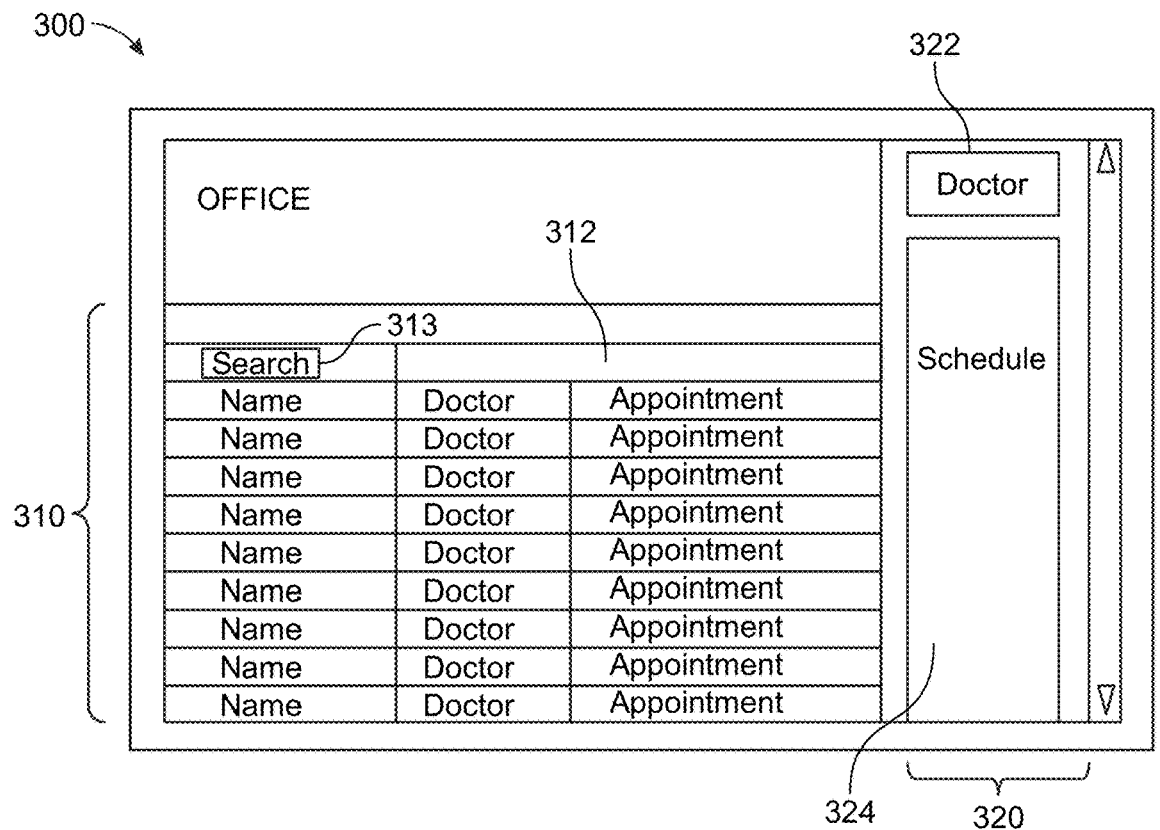
Figure 4:
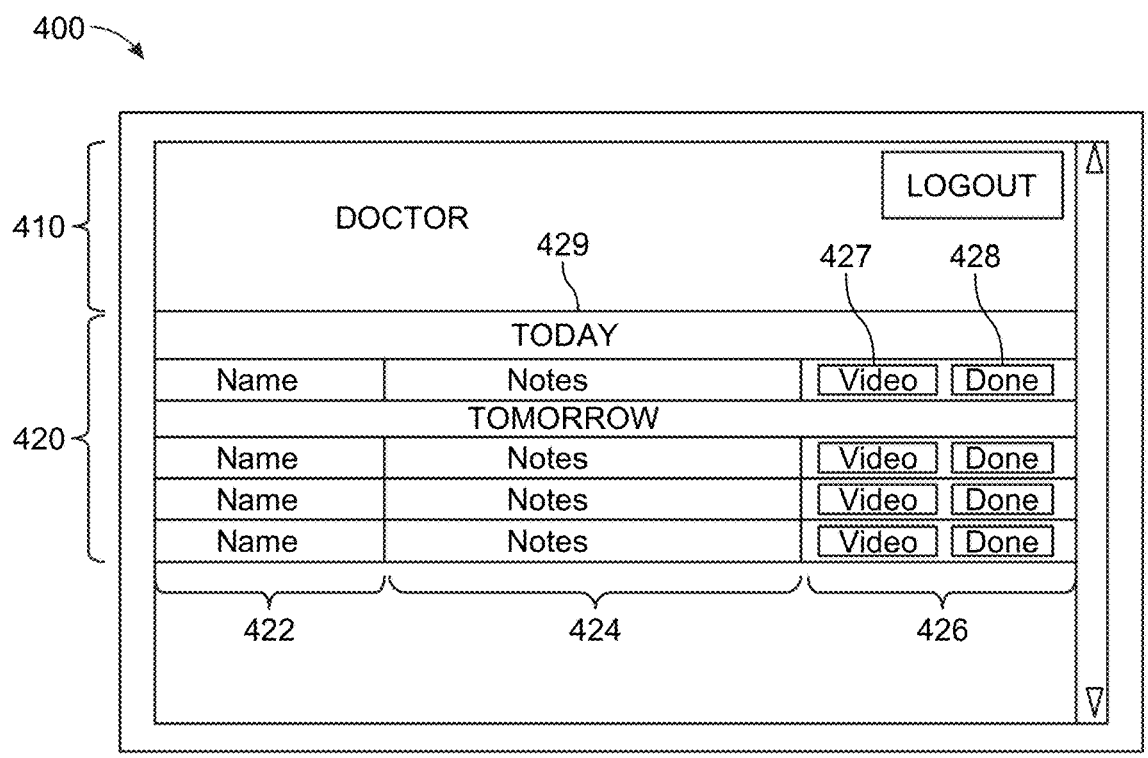

Turning now to FIGS. 2 through 4, where there are shown respective generalized schematic diagrams of examples of screen displays using a videoconferencing software application in accordance with the description herein. With regard to FIG. 2, a patient screen display 200 may generally be viewed by a patient using computing device 135 when running a videoconferencing software application.

As in FIG. 2, patient screen display 200 in this example is divided into two regions 210 and 220. Region 210 provides a one-touch link to the office of a treating physician. Activating this link, whether by mouse click, touchscreen or other action, may cause such videoconferencing software application to initiate a videoconference call to such physician's general office computing or other video conferencing device. This call may be answered by an office administrative assistant or other staff person, or a virtual administrative assistant. Such administrative assistant may then, for instance, assist such patient in setting up an appointment to conference with a physician or instruct such patient to wait before transferring such patient to videoconference with such physician by transfer of such call to the physician's computing or other video conferencing device.

Region 220 provides one-touch links to specific individuals which may include a patient's treating physician 222, primary care physician 224 or any specialists 226 involved in that patient's treatment. Activation of any of these links may directly initiate a conference call to a selected physician's computing device. Region 220 may include links to individuals 228 who have been diagnosed and/or treated for the same or similar medical condition afflicting a patient. Activation of any of these links may allow for social interaction between patients so as to form a virtual support group.

Additional pages may be displayed within a videoconferencing software application, including but not limited to a page wherein a patient can view a physician's schedule and thereby arrange an appointment for a videoconferencing, a page containing a digital copy of the patient's calendar showing upcoming appointments or other relevant information, and a page including links to journal articles or other items of news relevant to the patient's condition or treatment.

FIG. 3 depicts a generalized screenshot 300 of a videoconferencing software application, which may be viewed by administration personnel within a physician's office. Screen region 310 in this example displays a patient name, a treating physician name, and a scheduled appointment time, which may be in chronological and/or alphabetical order. A next client or patient appointment in time may be displayed as the top entry with each subsequent appointment listed below.

Box 312 is for entry of information regarding a patient in order to select box 313 to permit administrative personnel to search for a particular patient. Thus, if a patient Q cannot remember or locate for example the time of their next appointment, this example of a videoconferencing software application allows administrative person to search and locate that patient Q's next appointment date and time.

Region 320 may be used to display information specific to a particular physician/doctor. Box 322 may provide a dropdown menu wherein administrative personnel can select a particular doctor and have that doctor's daily schedule appear in box 324. Thus, if a patient contacts a doctor's office through a videoconference link, such as via activation of region 210, for an unscheduled conference, office personnel may determine if such doctor is free to engage in that conference or whether such doctor is otherwise occupied. Box 324 may be configured to allow office personnel to efficiently schedule appointments for various physicians within an office.

Turning now to FIG. 4, screen display 400 is an example of a username and password protected application page configured to be accessible only to a particular physician. Once logged onto their videoconference page, physician "DOCTOR", as shown in region 410, is presented with a listing of upcoming scheduled videoconference appointments as displayed in region 420.

Each horizontal patient line within region 420 provides a patient's name region or section 422 and time-day of appointment section 429. Optionally, a synopsis of relevant case information may be in notes section 424. Notes section 424 may be a type-in section wherein a physician can input notes regarding topics or areas to be discussed during a call.

A contact region 426 may have one-touch video activation links 427, which may be selected by mouse-clicked or touch operated for example. Such activation links 427 may be either initiate a videoconference call or consummate a videoconference call already initiated by a patient. Clicking or otherwise engaging a "Done" link 428 ends an associated videoconference. Optionally, selection of a video activation link 427 may instruct videoconferencing software application to save a copy of an associated videoconference to a remote server or other archive for later use or referral.

In an example of a PCH care delivery system 190, a microcontroller and microfluidics technologies may be used to provide a "smart" drug delivery device 180 for RTM and remote treatment of a patient.

Smart drug delivery devices can be segregated generally into three broad categories. A first category includes intravenous ("IV") smart delivery devices 180 may be used where a physician has direct access to a patient's bloodstream through an IV port. An IV smart delivery device 180 may be coupled to an IV port. IV smart delivery devices 180 provide for "immediate" administration of medication as these drugs are injected directly into the bloodstream and do not require diffusion through skin or other tissue. IV smart delivery devices 180 may be used for applications involving threats of severe and immediate loss of health, such as high risk heart attack or stroke patients. Additionally, CKD may be addressed separately, or along with at least one other disease, which may be comorbidity disease.

A second category of smart delivery devices 180 are configured for subcutaneous ("SC") administration. SC smart delivery devices 180 generally include large-scale needles of sufficient gauge and length to puncture and pass through skin and dispense drugs subcutaneously, such as for example in subcutaneous or hypodermis tissue, including a muscle layer, of a patient. SC smart delivery devices 180 may be used for conditions which involve periodic and/or "somewhat" immediate administrations. Injection of a drug for "somewhat" immediate administration means such drugs after injection are delivered at subcutaneous tissue but still must pass into the bloodstream of a patient. However, repetitive subcutaneous injections may lead to injection site pain and/or sensitivity. Such increased pain or sensitivity may lead to decreased patient compliance in using such a SC smart delivery device 180.

A third category of smart delivery devices are designed for transdermal ("TD") administration. Transdermal conventionally means absorption through skin. Examples of conventional transdermal patches are drug-impregnated adhesive patches which may be applied to skin of a patient for controlled release of such drug.

As described herein, a TD-like smart delivery device 180 may be used within a PCH care delivery system 190. TD-like smart delivery device 180 uses microneedles to penetrate skin to a depth passing through an outer skin moisture barrier layer and not exceeding 1 millimeter. By having such a shallow injection site, a moisture barrier of an outer skin layer may be passed through without impinging upon nerves located within a dermis layer of human skin. Thus, injections from TD-like smart delivery devices 180 are generally pain free. As such, a TD-like smart delivery device 180 may be suited for applications involving generally "non-immediate" and repeated dosing. By "non-immediate", it is generally meant that TD-like smart delivery device 180 administered drugs after injection must still pass or be absorbed through a dermis layer of tissue before entering a patient's blood stream.

To fully capitalize on each of IV, SC, and TD-like applications, smart delivery devices 180 may use multiple injection systems with multiple needles and multiple drug supply channels and reservoirs. More particularly, for reasons of compactness as well as to reduce patient discomfort, microneedles, microfluidics and microfluidic chips may be configured in a smart deliver device to deliver drugs in any one or more of the above-described contexts of IV, SC, and TD-like applications. Along those lines, microtubule arrays may be used as described herein to expand drug delivery from simply a one needle-one drug configuration to a one array-multiple drugs configuration.

Microtubule arrays may be mated to ensure fluid communication between a microtubule and a needle, whether an IV, an SC, or a TD-like microneedle. Such selection of microneedles and drugs may facilitate use of smart delivery devices 180 in combination drug therapy applications.

Figure 5A:
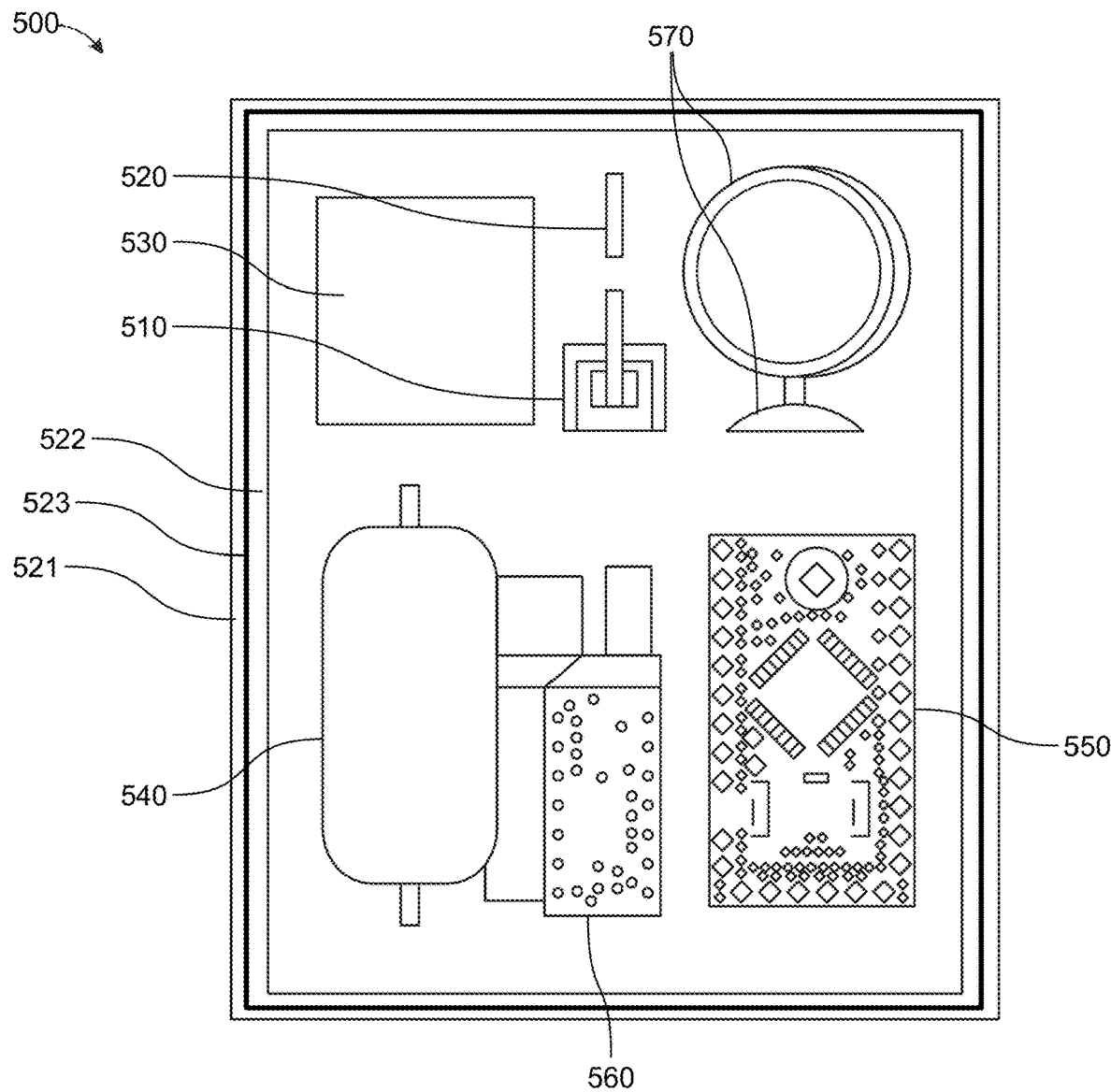
FIG. 5A is a pictorial diagram depicting an example of a transdermal-like wearable drug delivery device ("TD-like patch" or "smart patch").
Figure 5B:
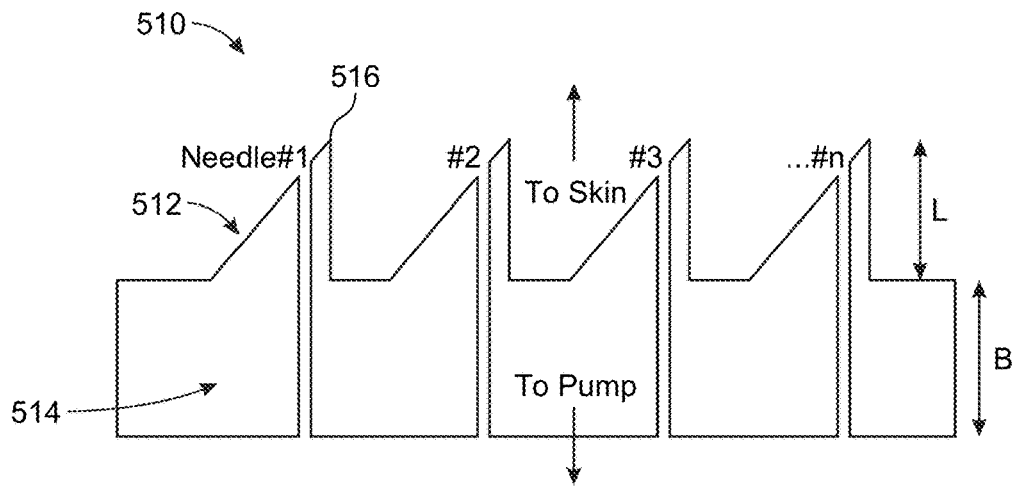
FIG. 5B is a schematic diagram depicting a cross-sectional side view of an array of microneedles of the TD-like patch of FIG. 5A.

FIG. 5A is a pictorial diagram depicting an example of a TD-like drug delivery device ("TD-like patch") 500. FIG. 5B is a schematic diagram depicting a cross-sectional side view of an array of microneedles 510 of TD-like patch 500 of FIG. 5A. TD-like patch 500 is further described with simultaneous reference to FIGS. 5A and 5B. TD-like patch 500 may be an example of a smart delivery device 180 for TD-like drug administration.

TD-like patch 500 has a bottom surface which is adapted to carry an array of microneedles 510, whereby such microneedles are position so as to puncture and pass through a moisture barrier outer skin layer when such patch is worn in direct contact with skin. Each microneedle 512 within array of microneedles 510 may have an out-of-plane design with a bore 514 of each needle displaced from an associated needle tip 516.

Each microneedle 512 may be configured to penetrate and exit an outer layer of skin without tissue or fluids plugging an associated bore 514. Microneedle length L may be selected to be between 100 microns and 500 microns, inclusive. More particularly, each microneedle length L may be selected to be between 150 microns and 350 microns. For purposes of clarity by way of example and not limitation, it shall be assumed that each microneedle has a length of approximately 350 microns.

The base of a microneedle array 510 which supports such microneedles has a thickness B. In this example, thickness B is approximately 250 microns. However, microneedle arrays may be constructed to have bases of this or any other suitable thickness depending on application and TD-like patch 500 configuration.

In this example, bore 514 may have a bore diameter of approximately 50 microns to 100 microns. For purposes of clarity by way of example and not limitation, a bore diameter of approximately 70 microns is described. Bore 514 extends proximate to tip 516, which may be through the entire length of a microneedle L and base B.

Each microneedle 512 may be serially selectively fed a medication for injection through a microfluidic channel 520. This medication may be pumped from a drug reservoir 530 through a microfluidic channel 520 by provision of dual-stage pump 540. In this example, dual-stage pump 540 is a micro piezo pump whose operation is controlled by microcontroller 550. Suitable drive electronics 560 may be used to manipulate channel 520 position relative to a particular microneedle 512 within a microneedle array 510. Microcontroller 550 may be configured to ensure that each microneedle 512 is used for a single injection only, namely a one-time use limitation.

Electrical components of TD-like patch 500 in this example may be powered by one or more batteries 570. TD-like patch 500 may be constructed as a two-piece system, wherein a reusable first piece includes microcontroller 550, drive electronics 560, and dual-stage pump 540, and wherein a disposable second piece contains the batteries 570, microfluidic channel 520, drug reservoir 530, and microneedle array 510. In another example, one or more batteries 570 may be rechargeable and be included in such reusable first piece.

Figure 6A:
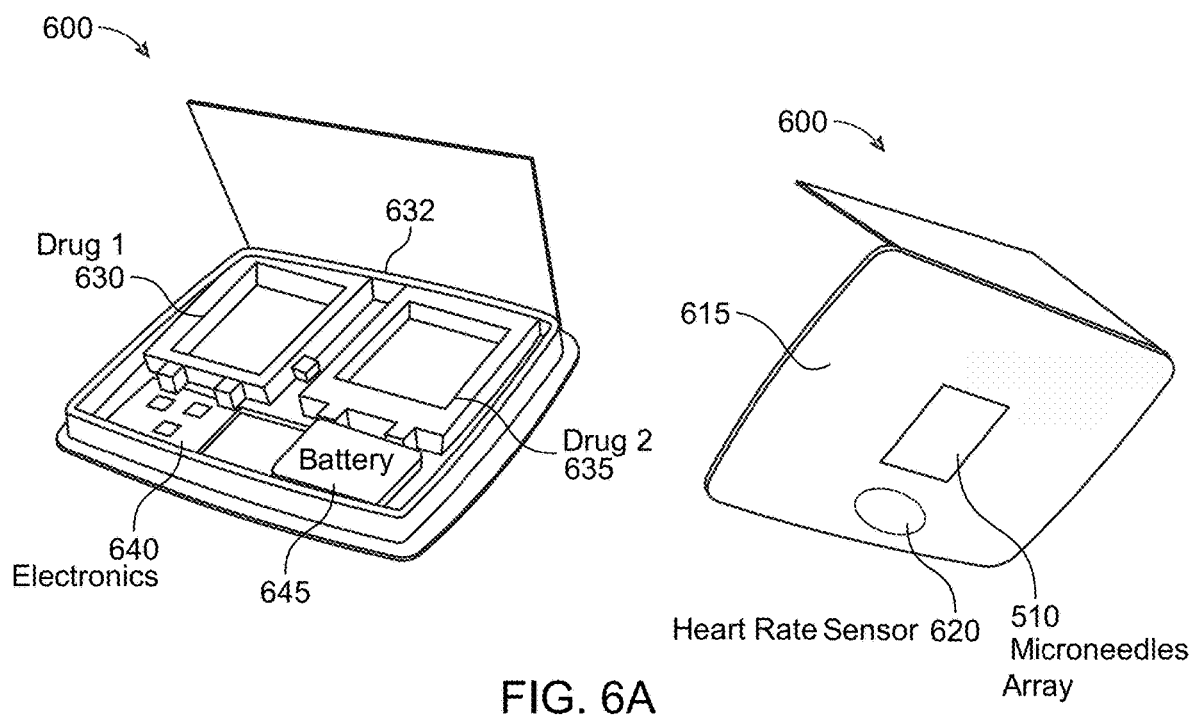
FIG. 6A is a pictorial diagram depicting an example of another TD-like patch

FIG. 6A is a pictorial diagram depicting an example of another TD-like drug delivery device ("TD-like patch") 600. As TD-like patches 500 and 600 have same or similar components, generally only differences are described hereinbelow for purposes of clarity and not limitation.

Effectively TD-like patch 600 is an expansion of TD-like patch 500 to include a dual channel design employing two drug reservoirs 630 and 635 and corresponding microfluidic channels 632. Respective microfluidic channels 632 deliver fluid from each drug reservoir to a particular microneedle within microneedle array 510. By employing more than one reservoir, TD-like patch 600 allows a physician to begin to introduce combination drug therapy by administration of two different drugs, each contained within its own reservoir. Optionally, one reservoir may contain a prescribed medication while another reservoir may contain a chemical enhancer to assist drug absorption, such as through the skin as described below in additional detail. Fluid flow may be controlled through micro-actuators, such as micro-linear actuators for example. However, in another implementation, respective dual-stage pump 540, such as micro piezo pumps, may be used.

A microcontroller, including associated electronics and programming thereof, ("microcontroller") 640 controls dispensing of drugs, with one or more batteries 645 supplying electrical power to electrical components of TD-like patch 600. Such a microcontroller 640 can be programmed to initiate dispensing of drugs from drug reservoirs 630 and/or 635 at respective predetermined dosages which may be at a same predetermine time interval or at different time intervals.

In this example, TD-like patch 600 includes a medical sensor 620. In this example, medical sensor 620 is a heart rate sensor. However, TD-like patch 600 may include more than one sensor 620 in other examples. For example, other types of sensors may include one or more temperature sensors, one or more moisture sensors, and/or one or more other types of sensors.

Microcontroller 640 may be preprogrammed by a physician or other medical profession. Data received by microcontroller 640 from one or more medical sensors 620. One or more of medical sensors 620 may wirelessly transmit data from such one or more sensors to microcontroller 640. Responsive to sensed data received by microcontroller 640, microcontroller 640 may activate a drug delivery mechanism upon a triggering event detected as indicated in such sensed data and/or a medical professional remote control thereof.

A dual channel design has a cost-effective two-layer construction with a reusable top or first layer piece including electronics, pump and rechargeable battery, and a disposable bottom or second layer housing including microfluidic delivery channels, microneedles, dual refillable drug reservoirs, and a soft rubber adhesive backing 615. TD-like patch 600 may be small, which in an example may have dimensions of approximately 5 cm wide by 0.6 cm long by 0.7 cm thick. Such a small size may be worn by a patient in a substantially non-intrusive manner. For example, such a small TD-like patch 600 may be worn under loose clothing. In another example, a small TD-like patch 600 may be refillable, in addition to having re-useable electronics, in a drug delivery vehicle patch.

Figure 6B:
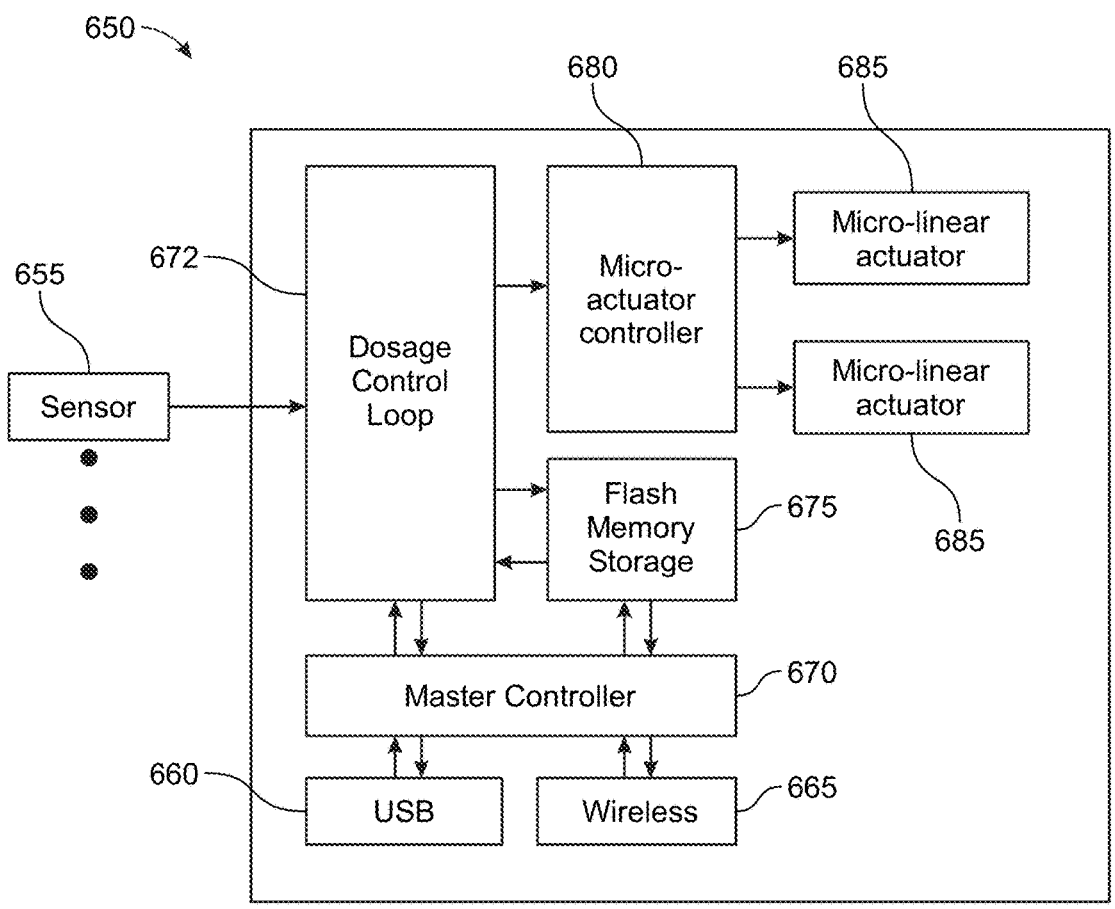
FIG. 6B is a pictorial diagram depicting an example of yet another TD-like patch.

FIG. 6B is a block diagram depicting an example of yet another TD-like drug delivery device ("TD-like patch") 650. TD patch 650 is a smart and highly-responsive multifunctional transdermal patch device with dosed loop feedback control that can provide a treatment that is dynamically tailored to patient's condition and input. Electronic control circuitry interfaces with dual micro-linear actuators for drug delivery.

In this example, a heart rate monitoring sensor and other sensor devices 655 communicate, which may include wired and/or wireless transmission of, real-time data to such TD-like patch 650. For purposes of clarity and not limitation, in this example transmission of data is through a wired connection 660, such as a USB connection for example, and/or via a wireless networking infrastructure, namely wireless interface 665. For instance, heart rate monitoring sensor data can be used to provide real-time adjustment to a drug delivery rate reflecting circadian rhythm adjustment throughout the day for minimum side effect and optimum impact based on an allowable range of therapeutic drug levels specified by a health provider's prescription. In this or another example, sensor devices 655 may include a hemoglobin sensor, such as one using a HemaApp or other technology using absorption properties of blood with respect to various wavelengths of light, generally from 400 nm to 1000 nm.

In contrast to TD-like patches 500 and 600, TD-like patch 650 replaces patch electronic control circuitry with a more advanced microcontroller 670. Microcontroller 670 runs firmware that contains an actuator control loop or dosage control loop 672 for dispensing one or more drug(s) to be administered. TD patch 650 may include contains a wired connection 660 and/or wireless interface 665. A chassis of patch 650 may have a chassis having a first frame 521 attached to a second frame 522 with electrical isolation/dielectric material 523 between such frames for proper functioning and as added protection against electrical shock.

In addition to communication with one or more wireless sensors, wireless interface may be used to facilitate remote communication with TD-like patch 650 such as for reconfiguration and programming of dosages. However, even though a physician or other medical professional may remotely operate a TD-like patch 650, operation of TD-like patch 650 may incorporate a closed loop feedback control based on sensor data. For example, such feedback control may incorporate a dosage loop process flow to adjust dosages by taking into account heart rate variable and circadian relationship, as well as hemoglobin level. Flash memory storage 675, which may be coupled between dosage control loop 672 and a microcontroller ("main" or "master" controller) 670, may be periodically store sensor readings and build a treatment history. Along those lines, a history of doses may be stored in flash memory storage 675 for use by an AI-based app, as described below in additional detail, a medical professional, and/or microcontroller 670 for dosage feedback control. TD patch 650 may contains additional components such as a micro-actuator controller 680 and one or more micro-actuators 685, as well as drug formulation reservoir(s) and microneedle array (not shown for clarity) but similar to those described above with regard to TD-like patch 600.

With additional reference to FIGS. 1 through 6B, when a smart phone or other smart device is in communication, such as through USB port or wirelessly, with a TD-like patch 650, patient feedback information, sensor data (e.g., heart rates, hemoglobin levels, among others), and delivered dosage data may be collected and securely uploaded from such smart phone or other smart device to a patient information database 115. Optionally, sensor and treatment data may be directly uploaded from TD-like patch 650 to patient information database 115 through wireless communication or indirectly through such smart device as previously described. Health care professionals can then review such updated patient data from such a database and, as determined such as for example on a situation-by-situation basis, remotely send a new treatment delivery profile directly to such a smart device. This updated delivery profile may be transferred to TD-like patch 650 for updating or reprogramming with such updated delivery profile. Such reprogramming may be subject to a next time such smart device is activated and in communication with TD-like patch 650; or such reprogramming may occur in a background mode without having a user activation of such smart device, where such smart device acts as a pass through mechanism to TD-like patch 650.

Through this feedback system, doctors may have the capability to remotely monitor patient status and remotely change, if needed, for example frequency and rate of drug delivery. In a further example, TD-like patch 650 may automatically deliver medications responsive to sensor readings indicating an immediate medical need. For instance, sensor 655 may record readings indicating a patient is potentially having a heart attack, kidney failure, or other serious heart or kidney disease issue. If these sensors readings correspond to a minimum threshold incorporated within a dosage loop process flow 672, microcontroller 670 can instruct micro-actuator controller 680 to cause one or both of linear micro-actuators 685 to dispense an immediate dosage of one or more medications to prevent or minimize damage due to such sensed potential heart attack, kidney failure, or other serious heart or kidney disease issue.

In utilizing conventional transdermal drug delivery systems, chemical enhancers are often used to assist diffusion of administered drugs through the skin to the bloodstream. Chemical enhancers such as oleic acid have been used for decades. Many such compounds, however, are toxic (such as DMSO or dimethyl acetamide). Furthermore, many of these enhancers are useful either only for a limited number of drugs or irritate the skin. More recently, combinations of non-toxic chemicals have been found that are effective for a wide variety of drugs without causing irritation. Normally the number of formulations to test was so large that it made testing mixtures difficult. However, a recent advance (impedance guided high-throughput screening) has made such testing feasible. Two particularly promising chemical enhancer mixtures are N-lauroyl sarcosine:sorbitan monolaurate (NLS:S20) and sodium laureth sulfate:phenyl piperazine (SLA:PP).

Additionally, conventional transdermal drug administration can be a function of time and a natural circadian rhythm. Indeed, the ability to deliver medication dosages that vary as a function of time, particularly to understand and effectively treat drug addiction, may be substantial. For some addictive drugs, such as heroin and cocaine, the very short time between administration and the resulting "peak" effects of the drug is a key contributor to their addictive nature. A smoker may light up a cigarette if they are feeling, for example, stressed at a particular moment. The physical and mental states of an addict—and the changes over time to those states—before, during, and after taking a drug are not able to be taken advantage of with current pharmacotherapies. This is because, on the time scales of interest, typically the delivery is effectively either only "instant" (e.g., a single intravenous injection) or constant (e.g., a passive transdermal patch). Similarly, a body's own responses change over the course of the day, as exemplified by circadian rhythms. Associated with these changes, different diseases seem to exhibit symptoms that rise and fall as a function of the time of day. Addictive behavior may be similarly affected.

Skin itself has a circadian rhythm, particularly for epidermal cell proliferation, perhaps due to its significant exposure to light. This is important to account for when designing transdermal drug delivery systems. Indeed, research has shown that nicotine clearances change by roughly 17% over the course of a day and 42% with meals. Researchers have concluded that because of time-dependent kinetic changes, an ideal transdermal system would provide an initial high delivery rate, near constant output during the day, decreasing delivery rate throughout the night, and short increases following meals.

Programmability, including without limitation remote reprogrammability, of a TD-like patch as described herein may allow such a patch to be programmed tailored to avoid or reduce possibility of addiction. An ability to perform combination drug therapy and incorporation of effective chemical enhances used with a TD-like patch as described herein may provide for more effective controlled delivery regimens in a variety of environments for treating a variety of diseases and other medical conditions, such as but not limited to drug addictions, obesity, and risk for kidney failure, heart attack or stroke.

Additionally, use of a TD-like patch as described herein may be used to save both time and money as: a patient does not have to be transported to a hospital for every potential condition; ER staff and doctors do not have to repeatedly readmit a patient each time the patient arrives at the hospital; insurance/Medicaid and hospitals save money by not readmitting patients but rather by treating at home/remotely; a PCDSS application saves physician time processing information and providing diagnoses/suggested courses of treatment; and/or physicians can effectively remotely monitor patients and modify treatment protocols or advise patients to become admitted to a hospital should the need arise. Use of a TD-like patch as described herein may save time and money as patients can receive prescribed medications through a smart delivery system allowing for combination drug therapy and remote reprogramming of such smart delivery device to modify or add medications without having to have an in person physician office visit.

Figure 7:
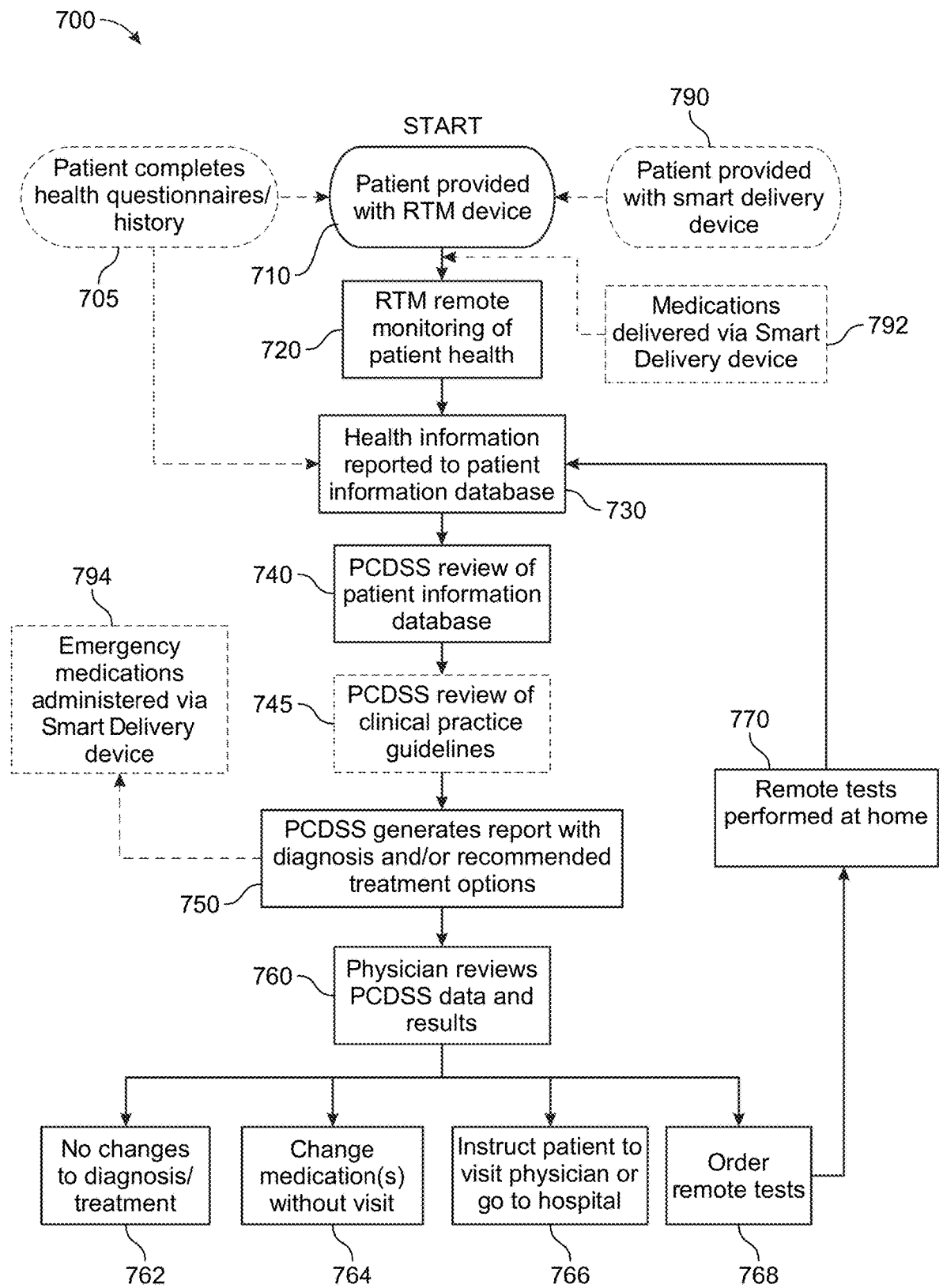
FIG. 7 is a flow diagram depicting an example of a PCH care delivery flow.

FIG. 7 is a flow diagram depicting an example of a PCH care delivery flow 700. PCH care delivery flow 700 may be used with PCH care delivery system 190, as previously described herein. PCH care delivery flow 700 is further described with simultaneous reference to FIGS. 1 through 7.

In operation 710, a patient may be provided with an RTM device 130 and instructed in its use. A patient may receive RTM device 130 following a check-up at a doctor's office or upon discharge from a hospital. RTM device 130 permits a patient to monitor their vital signs or other doctor-recommended health parameters (e.g., blood glucose levels, blood oxygenation, heart rate, blood pressure, hemoglobin level, etc.) from comfort of a patient's home or nursing facility at operation 720. As described above, in operation 730, RTM device 130 may be active for wireless communication with server 110, or transfer of information to an internet connected computing device, to provide immediate, real-time reading and recording of patient health statistics in a patient information database 115. A patient may optionally complete health questionnaires or medical history profiles at operation 705, and such questionnaire answer information may be stored within a patient information database 115.

In operation 740, a PCDSS interrogates patient information stored within a patient information database 115 to generate a report containing a preliminary diagnosis and/or a recommended course of treatment at operation 750. At least one of a patient diagnosis or a patient treatment recommendation may be generated for example based on an ICD 9/10 code by executing using a diagnostic computer application as described herein by computing device based upon real-time patient health information for at least one clinical practice guideline for at least one of: congestive heart failure for management of such congestive heart failure of and by a patient, or kidney failure for management of CKD of and by a patient.

At optional operation 745, a PCDSS can additionally access and utilize clinical practice guidelines ("CPGs") which pertain to a diagnosed condition (e.g., heart failure or kidney failure) as determined previously by a physician before a patient was released and provided with remote monitoring as in operation 710 or as determined by a PCDSS when analyzing a current patient health information. CPGs may help a PCDSS application, as well as a clinician, make medical decisions by providing recommendations that are based on various levels of evidence and are integrated with other clinical information systems that offer case-specific advice. Assisting a physician in diagnosis of complex diseases may involve a series of decisions that are often based on incomplete data. Thus, a process flow used in a PCDSS managed by a physician-centric healthcare network delivery system as described herein may be based on a combination of latest CPGs along with telemedicine to retrieve and monitor patient data on a daily basis.

Once a report is generated by a PCDSS at operation 750, a physician can access and review that report through a web-browser programmed computing device at operation 760. A notice or other electronic warning may be transmitted to a physician should a PCDSS determine a change in a patient's medical condition. For example, a patient diagnosed with congestive heart failure or kidney may be potentially about to suffer or may be currently suffering a heart attack or acute kidney failure. Depending upon a PCDSS analysis of a patient data, which may optionally include consultation to one or more CPGs, a PCDSS may recommend one or more of multiple courses of action. For instance, one recommendation may be to make no changes in a diagnosis or treatment regimen at operation 762; or a PCDSS can recommend modification to an administration of medication(s) without requiring an in-person visit at operation 764. A further recommendation may be to instruct a patient to schedule an appointment to see a physician in person or for a patient to go directly to a hospital at operation 766. A fourth recommendation at operation 768 includes an order for additional medical tests, with these tests being conducted by a home health professional at a patient's home, nursing facility or other location without requiring a patient to be readmitted to a hospital.

If remote tests are ordered and conducted as in operation 770, test results therefrom may be inputted into a patient information database 115. Such test results may then be analyzed by a PCDSS application to issue a further report. In each case, a treating physician may accept, modify or choose to ignore a PCDSS generated recommendation. While in this example only four recommended courses of action are shown, a PCDSS application may provide for any number of courses of action options that may be pertinent to proper treatment. A computing device may further store a scheduling computer application wherein execution of such scheduling computer application initiates a videoconference via an integrated telemedicine platform as described herein, where such telemedicine platform may be integrated with an E-prescription or other online prescription service, an online DME or other online equipment store, where shipping may be automated with drone, self-driving vehicle, Prime or Prime-like shipping, or other delivery service. Additionally, a patient may be informed of a Wellness Library or other library resource available online.

PCH care delivery flow 700 may further include provisions wherein a patient is provided with a TD-like smart delivery device 180, such as those described with reference to FIGS. 5A, 5B, 6A and 6B above. Optionally, such a smart delivery device 180 may further include IV or SC delivery systems. As shown in optional operation 790, in addition to being provided with an RTM device 130 at operation 710, a patient may be further provided with a smart delivery device 180. As indicated by operation 792, a smart delivery device administers medications, such as per physician instruction. A smart delivery device 180 may also, if indicated by a PCDSS 100 and sensed data, dispense an emergency dosage of medication to stop or minimize damage caused by an immediate medical crisis, such as a heart attack or kidney failure at operation 794.

A PCDSS software application may receive, interrogate and report a patient's medical condition in real-time from a patient's home, nursing care facility or other location through use of one or more RTM device 130(s). Use of a PCDSS software application may cut down on costly physician office or hospital emergency room visitation. Combined with abilities of portable remote medical diagnostic tools (e.g., portable x-ray, ultrasound, etc.) a PCDSS system allows a treating physician to readmit only those patients who require hospitalization. A treating physician may provide treatment of patients remotely, including medication modifications or remote testing, from comfort of that patient's home, nursing facility, or other location. A physician or other medical professional in charge may remotely instruct a patient via a diagnostic computer application, such as to reduce or discontinue use of a diuretic, to initiate or intensify dietary fluid restriction, or discontinue use of pain medications (e.g., aspirin, acetaminophen, ibuprofen, or naproxen sodium), by email, text message, voice recording, or other electronic delivery. Provision of a smart delivery device 180 may further aid in remote medicine by programmably and remotely re-programmably administering prescribed medications to patients, and further allows for immediate emergency dosing should a need arise, as previously described. Along those lines, automation as described herein may be used to improve care and drive down costs, including without limitation direct and indirect costs with the latter being due to readmissions. It is estimated that generally a call-center nursing staff may be reduced from 100 full-time nurses to less than 10 full-time nurses for care coordination.

By providing remote automated advice via message, emails, recorded voice and/or automated scheduling appointment to a patient to manage congestive heart failure or CKD, a more immediate potential heart or kidney failure may possibly be avoided or at least mitigated until direct physician assistance is available. Heart and kidney failures are a couple of the more costly issues due to difficulty of care coordination and people power. An implementation of a computing device configured to execute a diagnostic computer application may include processing of real-time patient health data from both Electronic Health Records (EHR) and Health Information Exchange (HIE) for a clinical practice guideline for congestive heart failure or kidney failure to generate a patient diagnosis or a patient treatment recommendation with a remote telehealth/telemedicine device for patient management of congestive heart failure or CKD; however, other medical conditions may benefit from this technology. Moreover, acute kidney failure often occurs in connection with another medical condition or event, including blood vessel blockages, diabetes, high-blood pressure, or heart failure, among others.

While the description herein is focused more on programming a smart delivery device 180 in a hospital or physician's office setting and then remotely monitoring such patient, including possibly remotely reprogramming such smart delivery device 180, use of smart delivery device 180 remotely with respect to a hospital is not required. In other words, a smart delivery device 180 may be used in a hospital room. As hospitals may be large campus-like facilities, an ability to remotely within a hospital facility to monitor and inject a patient may be useful.

Exemplary process flows scripted for use by a PCDSS as described with regard to PCH care delivery flow 700 for diagnosing and/or treating a patient with congestive heart failure ("CHF") is described with reference to example flow diagrams depicted in FIGS. 8 and 9. CHF may be merely exemplary and not limiting, and a PCDSS as described here can be utilized with regard to any suitable medical condition. Process flows used in a PCDSS for CHF managed by a physician-centric healthcare network delivery system are based on a combination of CPGs along with one or more RTMs to retrieve and monitor patient data on a periodic basis, such as one or more times per day for example. As an example, a patient's vital bio-data may be recorded and analyzed on a daily basis to establish a patient's normal baseline.

Any changes to a normal baseline, such as a rapid rise from a normal baseline in weight, heart rate, medication changes, and/or other baseline factor, could trigger a PCDSS application to: issue automated CHF detection alert to alert a physician to look for signs of CHF, and to quickly invoke an automated CHF management protocol. Adding patient vital bio-data monitoring and detection parameters increases a robustness of a PCDSS, allowing a physician to effectively manage one or more treatments for CHF patients which may result in a significant reduction in hospitalizations and readmissions thereof. For example, a PCDSS can automatically advise a patient to hold off on beta blocker medication (e.g., atenolol or metoprolol) when a PCDSS notices a patient's heart rate may be below 50 beats per minute, and in response, a PCDSS may send an automatic message to a physician network where a physician can then contact a patient.

As discussed above with regard to FIG. 7, a patient may be provided with an RTM device 130 to remotely monitor vital signs and other health data. For a patient with a history of one or more diseases, an RTM 130 may be used to monitor likely factors related thereto. For example, an RTM 130 may be used to measure a patient's heart rate, blood pressure, pulse oxygenation and other criteria as determined by a treating physician. In another example, RTM device 130 may be configured to accept demographics, facial input to a facial recognition system, date of birth for HIPAA, and other security enhancement.

A patient may additionally complete questionnaires regarding their health condition. This may include daily logs as to a level of fatigue felt by a patient, any shortness of breath or difficulty breathing or whether there may be swelling in one or more legs, each of which may be indicative of heart failure. Again, as described above, this data may be transmitted and stored within a patient information database 115.

A PCDSS via a CHF process flow may interrogate patient data to determine whether a patient may be suffering potential heart failure. If a patient's vital statistics or answers to questionnaires indicate heart failure, a CHF process flow may be initiated.

Figure 8:
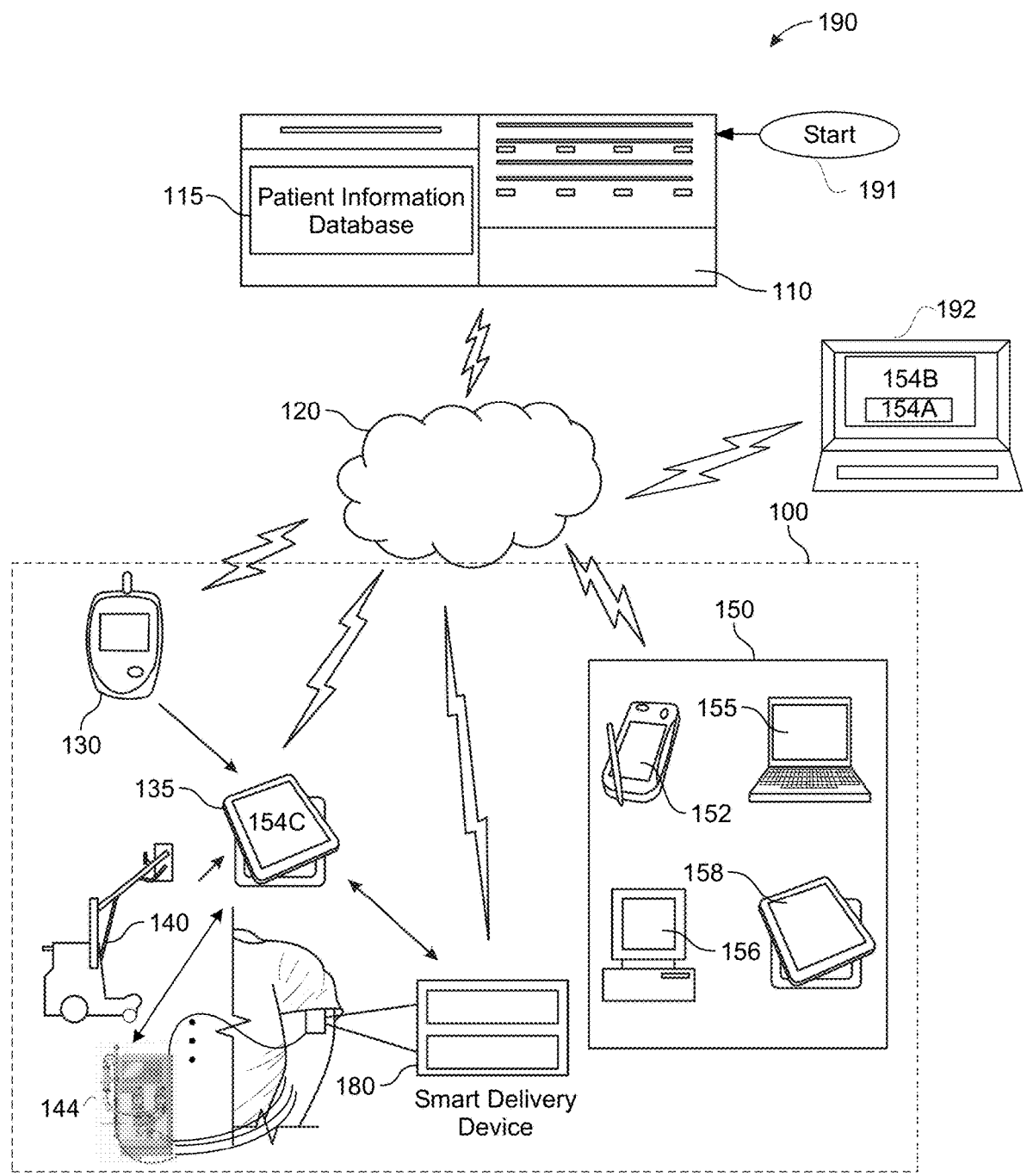
FIG. 8 is a pictorial-schematic diagram depicting another example of a PCH care delivery system.

FIG. 8 is a pictorial-schematic diagram depicting another example of a PCH care delivery system 190. As PCH care delivery system 190 of FIGS. 1 and 8 are similar in some respects, generally only differences between them are described below for purposes of clarity and not limitation.

By utilizing a web-based system, a treating physician can use a backend Cloud app, namely AI-driven PCDSS application ("AI-PCDSS app") 154B to access patient information database 115 via server 110 from any Internet accessible location. In this example, AI-PCDSS app 154B is a backend application programmed in whole or in part in a computer 192. Furthermore, in this example backend application, AI-PCDSS app 154B may include a chat bot 154A for soliciting and obtaining patient or medical professional input either or both by verbal communication or typing or pointing (e.g., a touchscreen input). Along those lines, a local, though less powerful, client AI-PCDSS app 154C may be another application used. AI-PCDSS app 154C may be a client or a client interface for access to a backend AI-PCDSS app 1546 running on a Cloud-based network, such as a backend application running in part on server 110. In this example, AI-PCDSS app 154C is configured to run on a tablet 135; however, in another example, another computation device as described herein may be used. However, for purposes of clarity and not limitation, AI-PCDSS apps 1546 and 154C are hereinafter collectively and singly referred to as AI-PCDSS app 154, subject to delineation as applicable. A chat bot 154A may communicate with a patient or a medical professional through a tablet 135 or other Internet of Things (IOT) device.

Furthermore, even though a computer 192 is used in this example, in another example another of Internet of Things (IOT) devices 150. To populate patient information database 115 with patient data, as well as to monitor and treat patients, each patient (for example a patient indicating kidney failure) may receive an RTM device 130. Again, an RTM device 130 may allow a patient to take their vital signs and other medical data (e.g., blood glucose levels, hemoglobin levels, blood pressure, oxygen saturation, weight, etc.), which may be in furtherance of a physician order. Obtaining such data may be from the comfort of a patient's home or residence or within a nursing care facility or hospital setting. Such data may be entered manually by a patient or may be measured and recorded automatically by RTM device 130.

RTM device 130 may be configured for wireless communication with server 110 for measurement and relaying of measured patient health data. Such data may be loaded onto a computing device or IoT devices 150 for uploading to such server 110. Examples of such computing devices include but are not limited to a smartphone 152, a laptop/notebook computing device 155, a desktop computing device 156, a tablet computing device 158, other smart devices or other suitable data hub device. IoT computing devices 150 may allow patients to complete online questionnaires regarding their health, as well as medical history. Examples of suitable IoT devices include a smart device, such as a smart medication patch or delivery device 180, home dialysis machine 144, smart phone/PDA 135, personal computer (PC) 156, a laptop computer (PC) 155, and tablet PC 158.

Using public-private key, private-private key, Kerberos, or other key exchange along with encryption, communications as described herein may be configured in a telemonitoring Physician-Centric system so that medication compliance can be monitored upon patients within a secure environment. Such security may be for patient privacy, as well as governmental regulatory compliance.

Such AI-PCDSS app 154 application assists physicians in providing an accurate diagnosis of a patient's medical condition based on patient data from such patient information database 115, which may include each patient's electronic health record (EHR) or Patient Health Record (PHR), periodic (e.g., daily, weekly, bi-weekly, monthly, etc.) data from an RTM device 130 and patient questionnaires/medical history. Relevant patient data from such patient information database 115 (patient history, previous encounter history, drug allergies, age, weight, etc.) and other updated daily data (heart rate, hemoglobin level, glomerular filtration rate (GFR), blood pressure (BP), weight, oxygen saturation, etc.) provide such input for a PCDSS analytical engine of AI-PCDSS app 154 to suggest appropriate diagnostic and treatment options that physicians can review and modify if needed.

In this example, a physician-centric health care delivery system or platform uses web-based applications that physicians can access anywhere through a wired or wireless connection, such as over the Internet, such as by Wi-Fi or ethernet for example, or by using a 4G/5G-enabled mobile devices, as previously described. A smart diagnostic and drug delivery medication patch ("smart patch") 180 in this example may be attached to a common injection site, such as at on the back or side of a patient's upper arm. Such smart patch 180 has a diagnostic and monitoring capability to count hemoglobin level and other vital signs, such as heart rate of a patient, which information may be sent through to a Cloud-based and/or other network 120 then to such server 110, and such information may be recorded in patient information database 115. Such information may be simultaneously sent or sent after recording to desktop computer 192 for AI-PCDSS app 154 for analysis of such hemoglobin level, among other data. AI-PCDSS app 154 may provide a corresponding diagnosis responsive to such received data, where such diagnosis is generated following AI-driven CKD management and assessment algorithms, examples of which are described below in additional detail.

Figure 9:
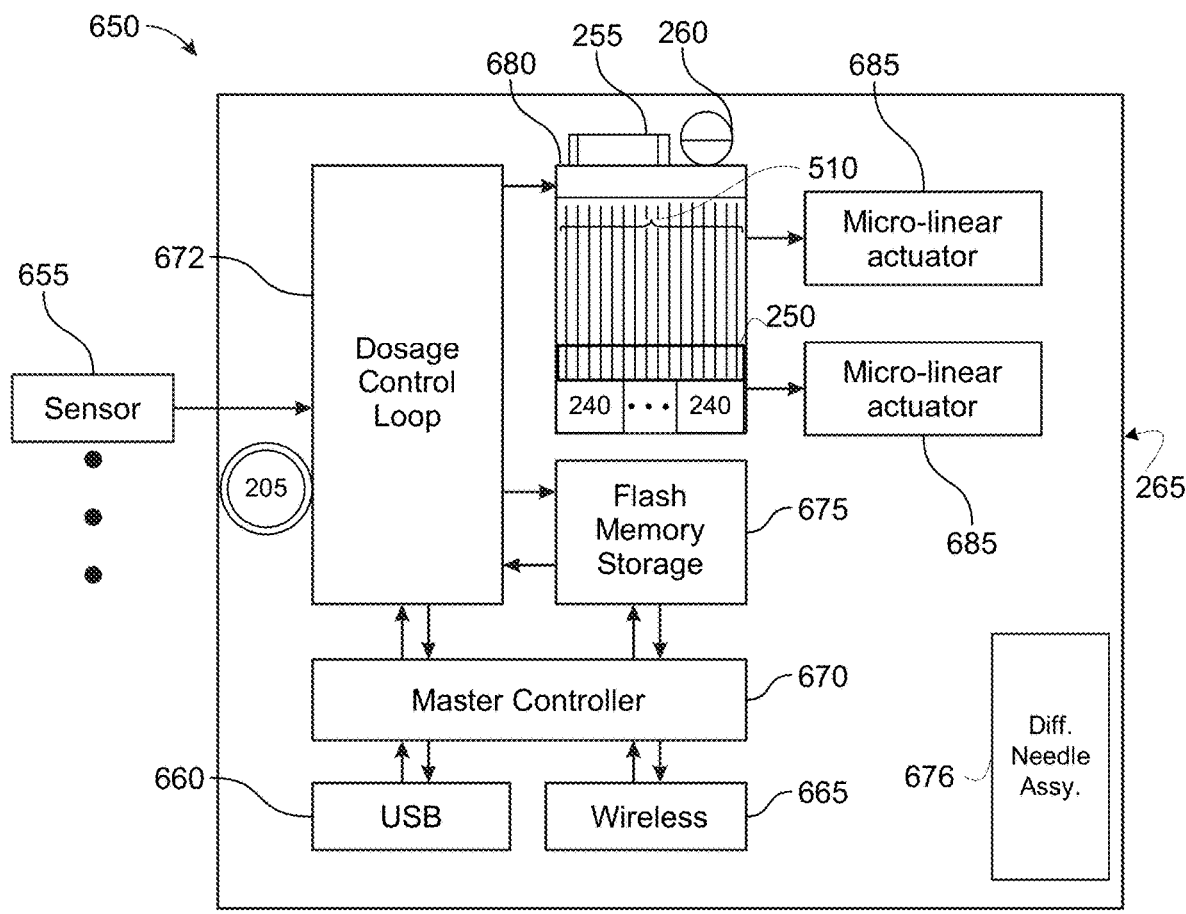
FIG. 9 is a block diagram depicting another example of a smart patch.

FIG. 9 is a block diagram depicting another example of a smart patch 650. Smart patch 650 of FIG. 9 may be an example of a smart patch 180 of FIG. 8. As smart patch 650 of FIGS. 6B and 9 have some same description, generally only differences are described below for purposes of clarity and not limitation.

A transdermal patch (TD) form may be used for smart patch 650. A TD smart patch 650 in this example has a channel design employing two drug reservoirs 240 and a hemoglobin count sensor 205. In this example, medical device' sensor 205 measures hemoglobin levels oximetrically; however, in another example sensor 205 may b configured to measure spectrophotometrically or via impedance measurement. In an example, sensor 205 may be configured to provides actual red cell counts or other measures of anemia such as ferritin levels. Smart patch 650 may be configured for automatic adjustment of dosage, such as of Epogen, responsive to a sensed hemoglobin count by sensor 205, where such adjustment may be performed in real-time.

Optionally, smart patch 650 may include an infusion needle assembly 676. Infusion needle assembly 676 may be removably attached, such as with a deployment mechanism actuated by a push button, for deployment within or from a housing of smart patch 650. Infusion needle assembly 676 may be for administering an emergency dosage in the event of improper functioning of smart patch 650.

Smart patch 650 may be a medium-sized smart patch, for example measuring approximately 7 cm×8 cm×0.9 cm. Smart patch may be wearable under loose clothing. Smart patch 650 may include refillable drug reservoirs and replaceable microneedle array 510 to provide a reusable electronics drug delivery vehicle.

Respective microchannels 250 in microfluidic communication with drug reservoirs 240 deliver fluid from each drug reservoir to a particular microneedle within one or more microneedle arrays 510. By employing more than one reservoir, such implementation of TD patch 650 allows a physician to begin to introduce a combination of a drug therapy by administration of two different drugs, each contained within its own reservoir. Alternatively, one reservoir may contain a prescribed medication while such second reservoir contains a chemical enhancer to assist drug absorption through such skin (as discussed in more detail below). Additionally, one or more assay capabilities may be provided as part of TD patch 650.

Fluid flow is controlled through micro-actuators, such as micro-linear actuators 685 in this example. However, in another example micro piezo pumps and/or micro actuators may be used. A multi-functioning smart medication patch 650 in this example has a tiny encrypted hemoglobin diagnostic sensor 205 combined with a transdermal drug delivery system channeled through microneedles to provide a dashboard-like monitoring system for a hemoglobin count resulting in an efficient delivery of Epogen or other biosimilars, as described below in additional detail.

A microcontroller and associated electronics 255 controls dispensing of drugs, with one or more rechargeable batteries 260 supplying electrical power to such patch components. Such microcontroller 235 can be programmed to initiate dispensing of drugs from one or more of drug reservoirs 240 at a corresponding predetermined dosage at a corresponding predetermined time interval.

TD smart patch 650 may be equipped with a hemoglobin count sensor 205. If preprogrammed, such as by a physician or other medical professional, data received by a microcontroller from such sensor (in other words, data transmitted from such sensor to such microcontroller) may cause such microcontroller to activate a drug delivery mechanism, such as smart patch 650. For example, upon a triggering event such as a hemoglobin level at a medical intervention level, detected by such sensor 205, smart patch 650 may trigger TD smart patch 650 to inject a medication, such as EPO for example. In this example of a smart patch 650, a dual channel design has a cost-effective two-layer construction with a first layer including electronics, pump and rechargeable battery, and a second disposable bottom layer housing such microfluidic delivery channels 250, microneedles 510, dual refillable or disposable drug reservoirs 240, and a soft rubber adhesive backing 265. Optionally, graphene oxide may be used instead of rubber as a coating material for a patch membrane material since it is thin and flexible, making it comfortable to wear on skin. Furthermore, when TD smart patch 650 is worn, one or more microneedles pierce skin when used, reaching subcutaneous tissue. For example, at 250 micrometer in diameter and 1 millimeter high, microneedles are too small to cause pain upon for injection into a patient. TD smart patch 650 in this example is a medium-sized patch, measuring approximately 7 cm×8 cm×0.9 cm, wearable under loose clothing, and is a refillable and reusable electronics drug delivery vehicle. However, other sizes, number of reservoirs, and other various configuration may be changed depending upon a patient's medical condition.

TD smart patch 650 may be used as a smart and highly-responsive multifunctional transdermal patch device with closed loop feedback control that can deliver a liquid medication that is dynamically tailored to patient's anemia diagnosis. Feedback control may be based on data from RTM 130 and hemoglobin count sensor 205. Electronic control circuitry, such as dosage control loop 672 and micro-actuator controller or microcontroller 680, may interface with dual micro-linear actuators 685 for drug delivery. In an example, a hemoglobin level detected by monitoring sensor 205 may transmit or otherwise communicate real-time data to TD smart patch 650 through a wired connection, such as via USB 660, or a wireless connection, such as via wireless interface 665, for such real-time data transmission. Furthermore, data may be provided via a SIM card for those who are outside an Internet hotspot. Dosage control loop and sensor 205 under control of a configured microcontroller 680 provide a sensing feedback loop to for PCHDS platform's with real-time updates to for micropump delivery, including adjustment and control of flow rate of liquid medication stored in one or more reservoirs 240. Along those lines, as hemoglobin count or level changes, flow rate may be adjusted accordingly in such feedback loop system.

Data transmission, whether instantaneous or with some latency, may include a hemoglobin count from sensor data of sensor 205, and such hemoglobin count can be used to provide real-time adjustments to a drug delivery rate. Such adjustments may be to reflect blood rate adjustment throughout each 24 hour or daily cycle. These adjustments may be to obtain a minimized side effect and an optimized impact based on an allowable range of therapeutic drug levels. Such a range of therapeutic drug levels may be based on a health provider's prescription informed through such AI-PCDSS 154, as in the context of supervised AI.

In contrast to conventional smart medication patches, TD smart patch 650 replaces such patch electronic control circuitry with a more advanced microcontroller 680. Such microcontroller runs firmware that contains such actuator control loop 672 for dispensing one or more drug(s) to be administered. TD smart patch 650 may contain a wired interface (e.g., USB) 660 and/or a wireless interface (e.g., Wi-Fi or Bluetooth) 665 to facilitate remote communication with smart patch 650 for reconfiguration and programming, including of dosages, which incorporates a closed loop algorithm. In accordance this example, such closed loop algorithm adjusts dosages by taking into account a hemoglobin count variable and other variable relationships as described below in additional detail. Flash memory storage 675 may be included to periodically store sensor 205 readings and build a treatment history. TD smart patch 650 may contain additional components, such as one or more micro-linear actuators 685, one or more drug formulation reservoirs 240, and a microneedle array 510.

In an example, a smart phone or other smart device may be connected, such as through USB port or wirelessly, to TD smart patch 650 to obtain patient feedback information, sensor data such as a hemoglobin count, a heart rate, and a delivered dosage. This data may be collected and securely uploaded from such smart phone/device to patient information database 115. Optionally or alternatively, this data may be directly uploaded from such TD smart patch 650 to such patient information database 115 through wireless communication.

Health care professionals, as well as AI-PCDSS app 154, can then review such updated patient data in such database and, if needed, remotely send a new delivery profile to such smart phone/device. This updated delivery profile may be transferred to smart patch 650 and activated such next time such smart phone/device is connected to such patch. Through this feedback system, doctors may have such capability to remotely monitor patient status and remotely change, if needed, such frequency and rate of drug delivery in such case of Epogen dosing to treat anemia. In a further example, TD smart patch 650 may automatically deliver medications upon sensor readings, such as when such sensor data indicates an immediate need for dosing. For instance, sensor 205 may record readings indicating a patient is having an abnormal hemoglobin count if such sensors readings correspond to a minimum threshold incorporated within a dosed loop algorithm, such as may be incorporated into dosage control loop 672. Microcontroller 680 may instruct one or more micro-linear actuators 685 to cause such micro-linear actuators to dispense an immediate dosage to prevent or minimize damage due to such sensed blood count abnormality.

A consideration to keep in mind when utilizing a transdermal drug delivery system is use of chemical enhancers to assist diffusion of administered drugs through skin into a bloodstream. Chemical enhancers, such as oleic acid for example, have been used for decades. However, many such compounds are toxic, such as DMSO or dimethyl acetamide. Furthermore, many of enhancers are useful either only for a limited number of drugs or irritate the skin. More recently, combinations of non-toxic chemicals have been found that are effective for a wide variety of drugs without causing irritation. Generally, the number of formulations to test was so large that it made testing mixtures difficult. However, a recent advance (impedance guided high-throughput screening) has made such testing feasible. Two particularly promising chemical enhancer mixtures are N-lauroyl sarcosine: sorbitan monolaurate (NLS:S20) and sodium laureth sulfate: phenyl piperazine (SLA:PP).

Programmability, including remote reprogrammability, such ability to perform combination drug therapy and incorporation of effective chemical enhancers used with transdermal patches disclosed herein may provide for more effective controlled delivery regimens in a variety of environments for treating a variety of diseases and other medical conditions, such as but not limited to drug addictions, obesity, and/or risk for heart attack or stroke.

Along those lines, both time and money may be saved as a patient does not have to be transported to a hospital for every potential condition. ER staff and doctors do not have to repeatedly readmit a patient each time a patient arrives at a hospital; insurance/Medicaid and hospitals save money by not readmitting patients but rather by treating at home/remotely; such AI-PCDSS app 154 can save a physician time by processing all relevant information and providing diagnoses/suggested courses of treatment; and physicians can still effectively monitor patients and modify treatment protocols or advise patients to become admitted to a hospital should such need arise. AI-PCDSS app 154 in combination with TD smart patch 650 further saves time and money as patients can receive prescribed medications through a smart diagnostic, monitoring and drug delivery system allowing for combination drug therapy and remote reprogramming of such device to modify or add medications without having to have a physician office visit.

Having described examples of systems, system platforms, and associated processes, an exemplary computer environment for implementing one or more aspects of one or more of the above-described examples is described.

Figure 10:
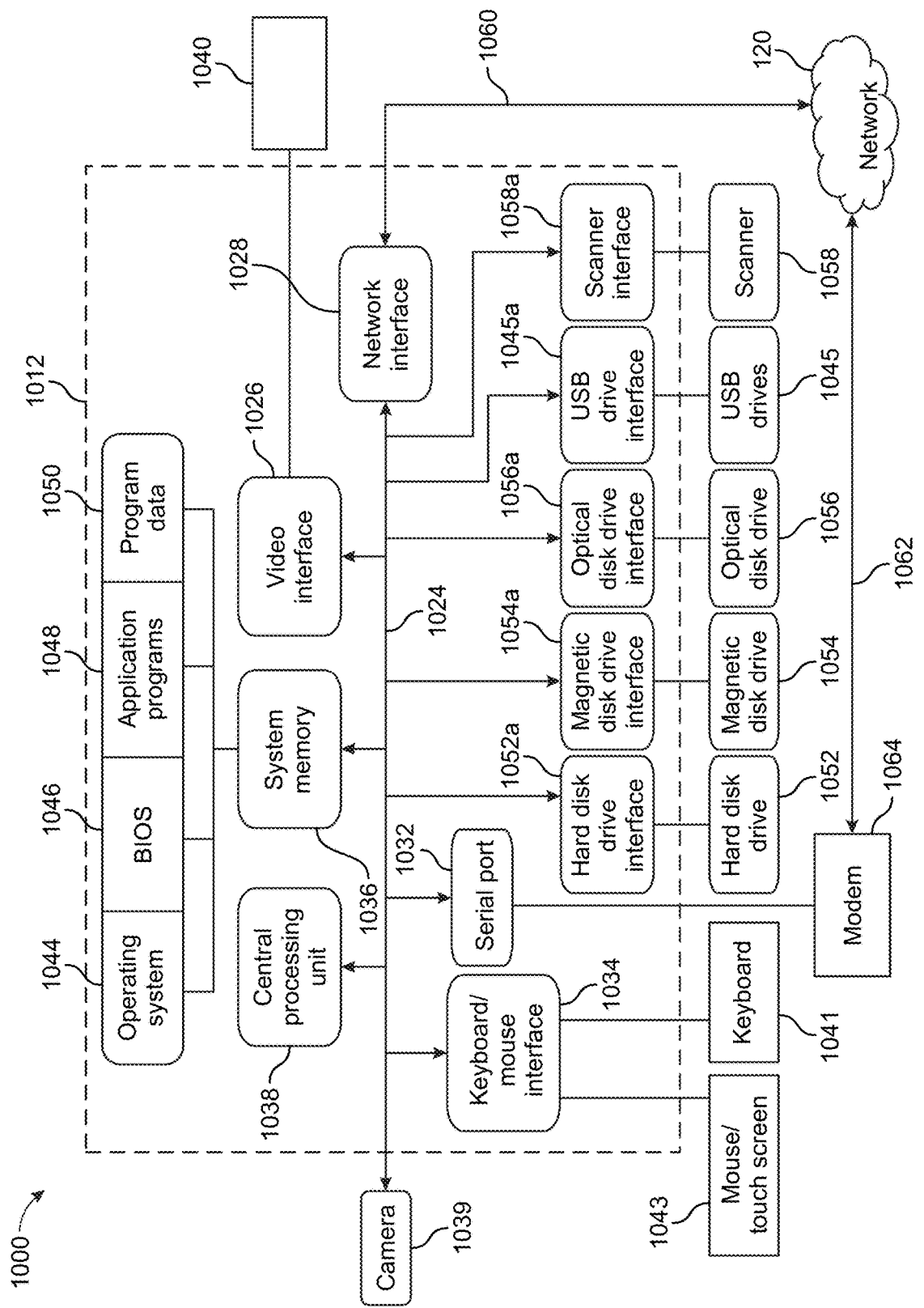
FIG. 10 is a block diagram depicting an example of a computing environment.

FIG. 10 is a block diagram depicting an exemplary computing environment 1000. Computing environment may be used to implement one or more aspects as previously described. Computing environment 1000 may include one or more computing devices 1012, such as any of computing devices 150 or 135. Computing environment may include a system bus 1024 that couples a video interface 1026, network interface 1028, a keyboard/mouse interface 1034, and a system memory 1036 to a Central Processing Unit (CPU) 1038.

A monitor or display 1040 may be connected to bus 1024 by video interface 1026 and may be used to provide display a graphical user interface that may be used by a user to perform operations of process flows 700, 800 and/or 900 as described above. A graphical user interface allows a user to enter commands and information into computing device 1012 using a keyboard 1041 and/or a user interface selection device 1043, such as a mouse, touch screen, or other pointing device. Keyboard 1041 and user interface selection device 1043 may be connected to bus 1024 through keyboard/mouse interface 1034. Additional interfaces may also be used, such as but not limited to PS/2 and USB interfaces, and the like.

A display 1040 and user interface selection device 1043 may be used in combination by a user for selection of one or more items displayed as a graphical user interface. In this or another example, display 1040 may be a touch-screen display.

Other peripheral devices may be connected to a remote computer through Universal Serial Bus (USB) drives 1045, fire wire, network interface, and the like to transfer information to and from computing device 1012. For example, a camera 1039 may be connected to computer 150 through serial port 1032, USB drives 1045, or to bus 1024 through other same or similar ports so as to allow video capture during videoconference calls. Additional interfaces may be used, such as but not limited to PS/2 and USB interfaces, and the like.

System memory 1036 may be connected to bus 1024 and may include read only memory (ROM), random access memory (RAM), an operating system 1044 stored therein, a basic input/output system (BIOS) 1046 stored therein, application programs 1048 stored therein, and program data 1050 stored therein. A computing device 1012 may further include a hard disk drive 1052 for reading from and writing to a hard disk, a magnetic disk drive 1054 for reading from and writing to a removable magnetic disk (e.g., floppy disk), an optical disk drive 1056 for reading from and writing to a removable optical disk (e.g., CD ROM or other optical media), a flash memory disk drive, and/or other long term data storage device.

A computing device 1012 may include USB drives 1045 and other types of drives for reading from and writing to flash memory devices (e.g., compact flash, memory stick/PRO and DUO, SD card, multimedia card, smart media xD card), and a scanner 1058 for scanning items to computing device 1012. A hard disk drive interface 1052a, magnetic disk drive interface 1054a, an optical drive interface 1056a, a USB drive interface 1045a, and a scanner interface 1058a operate to connect bus 1024 to hard disk drive 1052, magnetic disk drive 1054, optical disk drive 1056, USB drive 1045 and scanner 1058, respectively. Each of these drive components and their associated computer-readable media may provide remote computing device 1012 with non-volatile storage of computer-readable instruction, program modules, data structures, application programs, an operating system, and other data for computing device 1012. In addition, computing device 1012 may utilize other types of computer-readable media in addition to those types set forth herein, such as digital video disks, random access memory, read only memory, other types of flash memory cards, magnetic cassettes, and a like.

Computing device 1012 may operate in a networked environment using logical connections with other computing devices. Network interface 1028 provides a communication path 1060 between bus 1024 and internet/network 120, which allows, for example, an RTM device 130 or patient programmed home computer or other programmed computing device to communicate data to a patient information database 115 via server 110, as well as allowing physicians to access a patient information database 115 via in part computing device 150. This type of logical network connection may be commonly used in conjunction with a local area network (LAN) or another network topology. Patient information files may be communicated from bus 1024 through a communication path 1062 to internet/network 120 using serial port 1032 and a modem 1064. Using a modem connection between a computing device 1012 and other computing devices in a network may be commonly used in conjunction with a wide area network (WAN). Network connections shown herein are merely exemplary, and accordingly these or other types of network connections between computing device 1012 and one or more other computing devices, including both wired and/or wireless connections, may be used.

Figure 11:
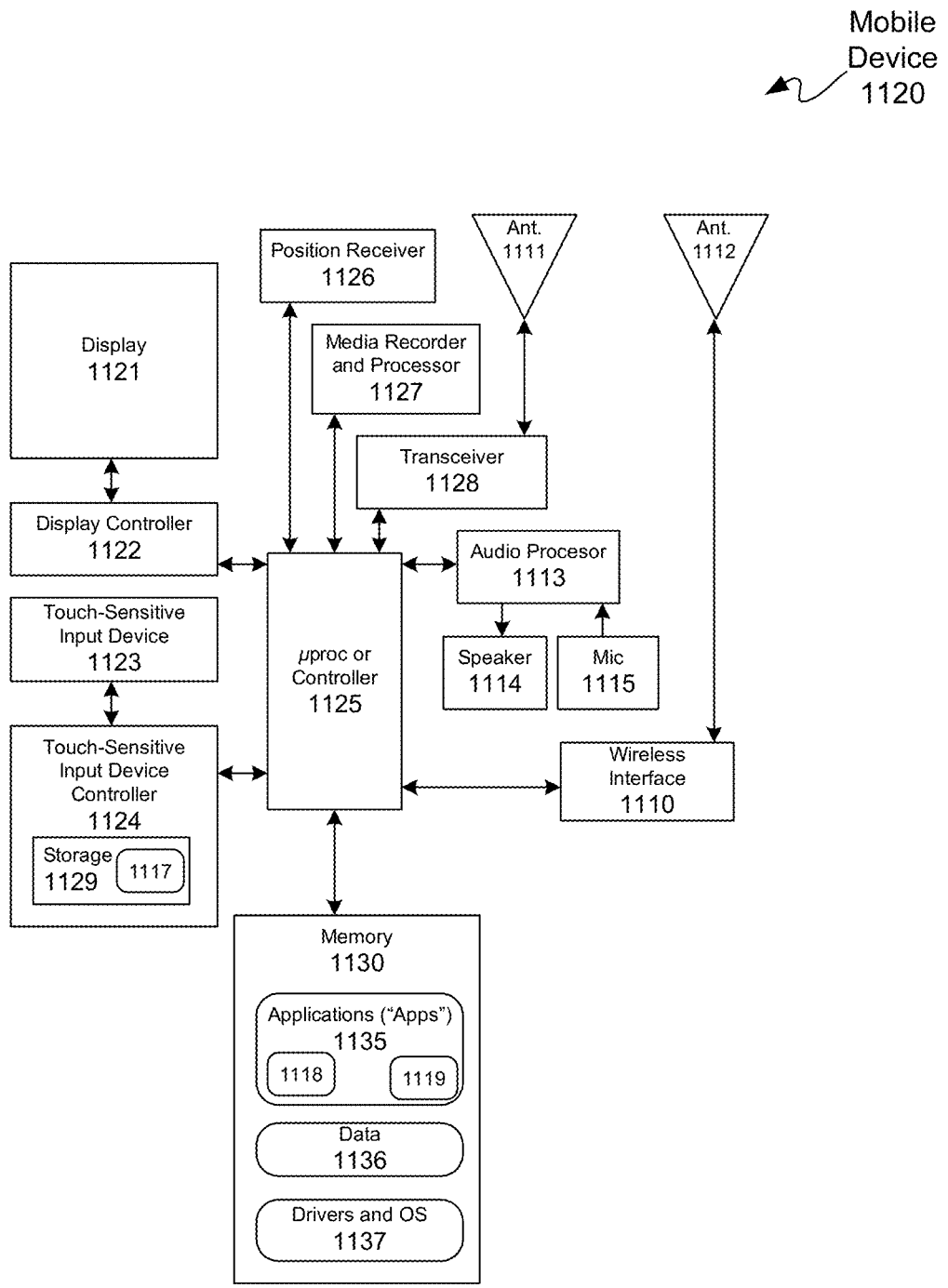
FIG. 11 is block diagram depicting an example of a portable communication device ("mobile device").

FIG. 11 is block diagram depicting an exemplary portable communication device ("mobile device") 1120. Mobile device 1120 may include a wireless interface 1110, an antenna 1111, an antenna 1112, an audio processor 1113, a speaker 1114, and a microphone ("mic") 1115, a display 1121, a display controller 1122, a touch-sensitive input device 1123, a touch-sensitive input device controller 1124, a microprocessor or microcontroller 1125, a position receiver 1126, a media recorder 1127, a cell transceiver 1128, and a memory or memories ("memory") 1130.

Microprocessor or microcontroller 1125 may be programmed to control overall operation of mobile device 1120. Microprocessor or microcontroller 1125 may include a commercially available or custom microprocessor or microcontroller.

Memory 1130 may be interconnected for communication with microprocessor or microcontroller 1125 for storing programs and data used by mobile device 1120. Memory 1130 generally represents an overall hierarchy of memory devices containing software and data used to implement functions of mobile device 1120. Data and programs or apps as described hereinabove may be stored in memory 1130.

Memory 1130 may include, for example, RAM or other volatile solid-state memory, flash or other non-volatile solid-state memory, a magnetic storage medium such as a hard disk drive, a removable storage media, or other suitable storage means. In addition to handling voice communications, mobile device 1120 may be configured to transmit, receive and process data, such as Web data communicated to and from a Web server, text messages (also known as short message service or SMS), electronic mail messages, multimedia messages (also known as MMS), image files, video files, audio files, ring tones, streaming audio, streaming video, data feeds (e.g., podcasts), and so forth.

In this example, memory 1130 stores drivers, such as I/O device drivers, and operating system programs ("OS") 1137.

Memory 1130 stores application programs ("apps") 1135 and data 1136. Data may include application program data.

I/O device drivers may include software routines accessed through microprocessor or microcontroller 1125 or by an OS stored in memory 1130. Apps, to communicate with devices such as the touch-sensitive input device 1123 and keys and other user interface objects adaptively displayed on a display 1121, may use one or more of such drivers. For example, a driver may be used for communication from keys of a user interface displayed on display 1121 associated with touch zones of touch sensitive input device 1123. Moreover, drivers may be used for other actual or virtual input/output ports of mobile device 1120.

Mobile device 1120, such as a mobile or cell phone, may include a display 1121. Display 1121 may be operatively coupled to and controlled by a display controller 1122, which may be a suitable microcontroller or microprocessor programmed with a driver for operating display 1121.

Touch-sensitive input device 1123 may be operatively coupled to and controlled by a touch-sensitive input device controller 1124, which may be a suitable microcontroller or microprocessor. Along those lines, touching activity input via touch-sensitive input device 1123 may be communicated to touch-sensitive input device controller 1124. Touch-sensitive input device controller 1124 may optionally include local storage 1129 for storing locations or touch zones or other location information 117 associated with touching activity input. In another example, location information 117 may be stored in memory 1130.

Touch-sensitive input device controller 1124 may be programmed with a driver or application program interface ("API") for output of location information 117 to an app 118 of apps 1135. In another example, app 118 may be incorporated into OS 1137. One or more aspects of above-described apps may operate in a foreground or background mode.

In an example, touch-sensitive input device 1123 is configured to facilitate touch input functionally, namely detection of user touch of an upper surface of display 1121 and touch-sensitive input device 1123 combination and recognition of user input based on locations of such touching activity. Such touching activity may be discrete touches and/or swipes. Further, touch-sensitive input device controller 1124 may be configured to provide haptic feedback features associated with such touch-sensitive input device 1123. Functionality of touch-sensitive input device controller 1124 may be carried out via dedicated hardware, firmware, software, or combinations thereof.

Microprocessor or microcontroller 1125 may be programmed to interface directly touch-sensitive input device 1123 or through touch-sensitive input device controller 1124. Microprocessor or microcontroller 1125 may be programmed or otherwise configured to interface with one or more other interface device(s) of mobile device 1120. Microprocessor or microcontroller 1125 may be interconnected for interfacing with a transmitter/receiver ("transceiver") 1128, audio processing circuitry, such as an audio processor 1113, and a position receiver 1126, such as a global positioning system ("GPS") receiver. An antenna 1111 may be coupled to transceiver 1128 for bi-directional communication, such as cellular and/or satellite communication.

Mobile device 1120 may include a media recorder and processor 1127, such as a still camera, a video camera, an audio recorder, or the like, to capture digital pictures, audio and/or video. Microprocessor or microcontroller 1125 may be interconnected for interfacing with media recorder and processor 1127. Image, audio and/or video files corresponding to the pictures, songs and/or video may be stored in memory 1130 as data 1136.

Mobile device 1120 may include an audio processor 1113 for processing audio signals, such as for example audio information transmitted by and received from transceiver 1128. Microprocessor or microcontroller 1125 may be interconnected for interfacing with audio processor 1113. Coupled to audio processor 1113 may be one or more speakers 1114 and one or more microphones ("mic") 1115, for projecting and receiving sound, including without limitation recording sound, via mobile device 1120. Audio data may be passed to audio processor 1113 for playback. Audio data may include, for example, audio data from an audio file stored in memory 1130 as data 1136 and retrieved by microprocessor or microcontroller 1125. Audio processor 1113 may include buffers, decoders, amplifiers and the like.

Mobile device 1120 may include one or more local wireless interfaces 1110, such as a WiFi interface, an infrared transceiver, and/or an RF adapter. Wireless interface 1110 may provide a Bluetooth adapter, a WLAN adapter, an Ultra-Wideband ("UWB") adapter, and/or the like. Wireless interface 1110 may be interconnected to an antenna 1112 for communication. As is known, a wireless interface 1110 may be used with an accessory, such as for example a hands-free adapter and/or a headset. For example, audible output sound corresponding to audio data may be transferred from mobile device 1120 to an adapter, another mobile radio terminal, a computer, or another electronic device. In another example, wireless interface 1110 may be for communication within a cellular network or another Wireless Wide-Area Network (WWAN).

As previously described, mobile device 1120 may be configured to provide communication as associated with one or more apps. Such communication may be to a Cloud-based system and/or to a smart delivery device 180. Along those lines, mobile device 1120 may be configured to provide one or more portions of an RTM device 130, a programmed computing device 150, and/or a computing device 135 for a PCDSS 100 of a PCH care delivery system 190 of FIG. 1.

Figure 12:
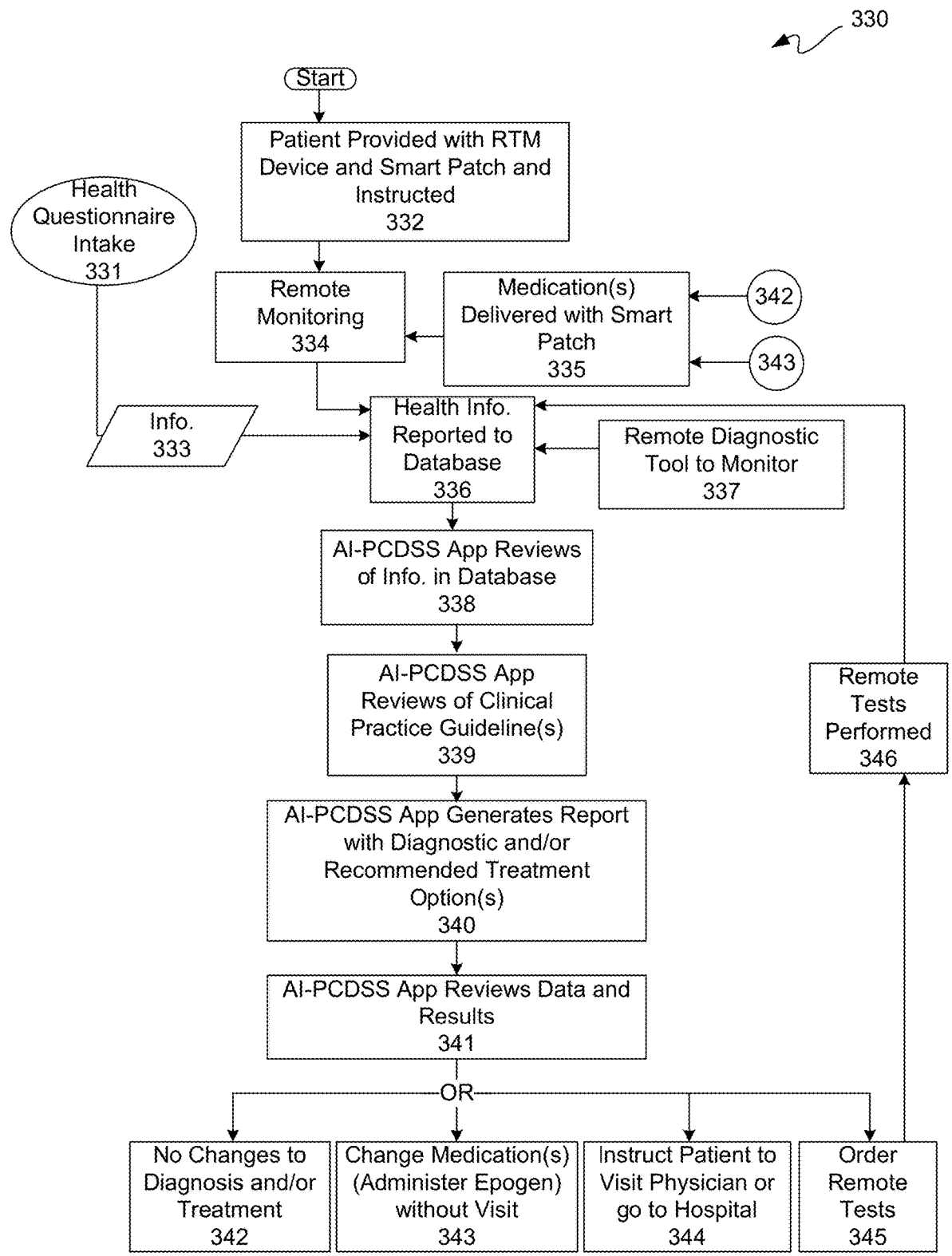
FIG. 12 is a flow diagram depicting an exemplary treatment delivery flow for the PCH care delivery system of FIG. 8.

As previously indicated, remote monitoring may be used to detect early stages of CKD through AI. Having described examples of components and aspects that may be included in PCH care delivery system 190, FIG. 12 is a flow diagram depicting an exemplary treatment delivery flow 330 for PCH care delivery system 190. Treatment delivery flow 330 is further described with simultaneous reference to FIGS. 1 through 12.

At operation 332, a patient is provided with an RTM device 130 and a smart patch 650 and instructed in their use. Such patient may receive such RTM device 130 and smart patch 650 following a check-up at a doctor's office or upon discharge from a hospital. Such RTM device permits such patient to monitor their vital signs or other doctor-recommended health parameters (e.g., blood glucose levels, blood oxygenation, hemoglobin count, heart rate, blood pressure, among others) from the comfort of such patient's home or nursing facility at operation 334. Such RTM device 130 and smart patch 650 provided at operation 332 may be configured and activated for wireless communication with server 110 and/or for transfer of information to an Internet connected computing device to provide immediate, real-time reading and recording of patient health statistics with patient information database 115.

A patient may optionally complete health questionnaires and/or medical history profiles at operation 331. At operation 336, such information 333 obtained at operation 331 may be stored within patient information database 115 for subsequent access. Additionally, such information may be supplemented with frequent monitoring at operation 337 with a separate remote diagnostic tool, as an optional addition to remote monitoring at operation 334.

In operation, a smart diagnostic and drug delivery medication patch provided to a patient at operation 332 has capability to diagnose and monitor patient's hemoglobin count and other vital signs or other doctor-recommended health parameters such as heart rate, blood pressure, blood glucose levels, hemoglobin count, among others in real-time. This information or data may be frequently obtained at operations 334 and/or 337, including obtaining a hemoglobin count with sensor 205, and such information may be provided to a patient database at operation 336. Furthermore, more recent information may be locally stored, such as in RTM 130 and/or smart patch 650. With respect for example to hemoglobin count, home dialysis machine 144 may optionally be connected to a patient, as is known, and may additionally be connected to TD smart patch 650, such as via a USB port for example.

Such smart diagnostic and drug delivery medication patch 650 may administer medications such as Epogen at operation 335 to treat CKD patients with anemia as per AI-PCDSS app 154 instruction as supervised by a physician. Such treatment may be responsive to continued monitoring, such as at operation 334, of hemoglobin count with sensor 205 for response to an administered medication, such as for example Epogen. If, however, Epogen does not seem to be substantially addressing the anemia, home dialysis machine 144 may optionally be used under control of TD smart patch 650.

At operation 338, such AI-PCDSS app 154 may interrogate such patient information stored within such patient information database at operation 336 to generate a report containing a preliminary diagnosis and/or a recommended course of treatment at operation 340. In an interim between operations 336 and 340, at operation 339, such AI-PCDSS app 154 can optionally additionally access and utilize Clinical Practice Guidelines ("CPGs") which pertain to such diagnosed condition (e.g., CKD with anemia) as determined previously by a physician or with physician supervised AI-PCDSS app 154.

For example, before a patient is released with a provided RTM 130 and a smart patch 650 at operation 332, a physician determined diagnosis, which may be determined by physician supervised AI-PCDSS app 154 including analyzing such current patient health information at operation 336, may access one or more CPGs. Along those lines, such one or more CPGs may be optionally accessed by AI-PCDSS app 154 at operation 339 in addition to access to data at operation 336 by such AI-PCDSS app 154.

CPGs help clinicians, as well as AI-PCDSS app 154, make medical decisions by providing recommendations that are based on various levels of evidence and are integrated with other clinical information systems that offer case-specific advice. Assisting such physician in diagnosis of complex diseases requires a series of decisions that are often based on incomplete data. Thus, AI-PCDSS app 154 used in such PCDSS managed by such physician-centric healthcare network delivery system as described herein may be based on a combination of the latest CPGs along with telemedicine to retrieve and monitor patient data on a daily basis.

AI-PCDSS app 154 receives, interrogates and reports a patient's medical condition in real-time from such patient's home or nursing care facility through such use of one or more RTM device(s) 130 without necessarily having to have a costly physician office or hospital emergency room visitation. Combined with such ability of such smart patch 650 with hemoglobin count sensor 205 and other monitoring sensors, such PCDSS system allows a treating physician to readmit only those patients who may require hospitalization, while also allowing further treatment of patients (through medication modifications or remote testing) from the comfort of such patient's home or nursing facility. Provision of a smart delivery device further aids in remote medicine by programmably, including remote reprogrammability for, administering prescribed medications to patients therefore promoting medication compliance to CKD patients with anemia who are in a lifetime dependency on dialysis, such as may involve an Epogen treatment.

Exemplary algorithms scripted for use by AI-PCDSS app 154 as described with regard to treatment delivery flow 330 for diagnosing and/or treating CKD patients with anemia are described below with reference to FIGS. 13 through 17. In this example, such algorithms used in such PCDSS for CKD with anemia managed by such physician-centric healthcare network delivery system are based on a combination of the latest CPGs along with RTM device 130 and smart patch 650 to retrieve and monitor patient data on a daily or other frequent basis.

For example, a patient's vital bio-data may be recorded and analyzed on a daily basis to establish a patient's normal baseline. Operations 336 through 340 may be performed on an ongoing basis for such daily basis, where operations 334 and optionally 337 are continuously performed at a selected or input frequency. Any changes to such normal baseline, such as a rapid rise from such normal baseline in hemoglobin level, heart rate, or other rapid change, may trigger such AI-PCDSS app 154 to issue a CKD detection and alert to a physician to look for signs of CKD at different stages and quickly automate such CKD management protocol. Adding patient vital bio-data monitoring and detection parameters increases robustness of such PCDSS and allows a treating physician to effectively manage such treatments for CKD patients which may result in a significant reduction in hospitalizations and readmissions.

Based on such information and one or more CPGs, at operation 340 AI-PCDSS app 154 may generate a report with a diagnosis and/or recommended treatment options. In an example, an initial report may be generated by AI-PCDSS app 154C at operation 340, an AI-PCDSS app 154B can access and review such locally generated report at operation 341. A supervising physician or other medical profession, through an Internet configured computing device, may supervise AI-PCDSS app 154B in concurring, modifying, or other adjusting or changing of such locally generated report. Along those lines, a notice or other electronic warning may be transmitted to a supervising physician should such PCDSS app 154B determine a change in a patient's medical condition, such as for example a patient diagnosed with CKD potentially about to suffer or currently suffering from anemia as a complication of such disease.

Depending upon such AI-PCDSS app 154 analysis of patient data possibly with optional consultation to one or more CPGs, AI-PCDSS app 154 may provide a recommendation of one or more of a multiple courses of action. For instance, one recommendation AI-PCDSS app 154 may provide is to make no changes in a current diagnosis or treatment regimen at operation 342. Another recommendation AI-PCDSS app 154 may provide is to recommend modification to a current regimen of administration of medication(s), such as Epogen, without requiring an in-person visit at operation 343. Yet another recommendation AI-PCDSS app 154 may provide is to instruct such patient to schedule an appointment to see a nephrologist in person or for such patient to go directly to a hospital at operation 344. Still yet another recommendation AI-PCDSS app 154 may provide is to an order one or more additional medical tests at operation 345. Such additional tests may be conducted by a home health professional at such patient's home, nursing facility or other location without requiring such patient to be readmitted to a hospital.

If remote tests are ordered and conducted at operation 346, such test results may be input into a patient information database 115 at operation 336, and such input test results may be reviewed and analyzed by such AI-PCDSS app 154 at operation 338 to issue a further or updated report. In each instance, a treating physician may accept, modify or choose to ignore such AI-PCDSS app 154 generated recommendations. It is understood that, while in such example only four recommended courses of action constituting operation 342 through 345 are shown, such AI-PCDSS app 154 may provide one or more of these and/or one or more other recommended courses of action options that may be pertinent to proper treatment.

Figure 13:
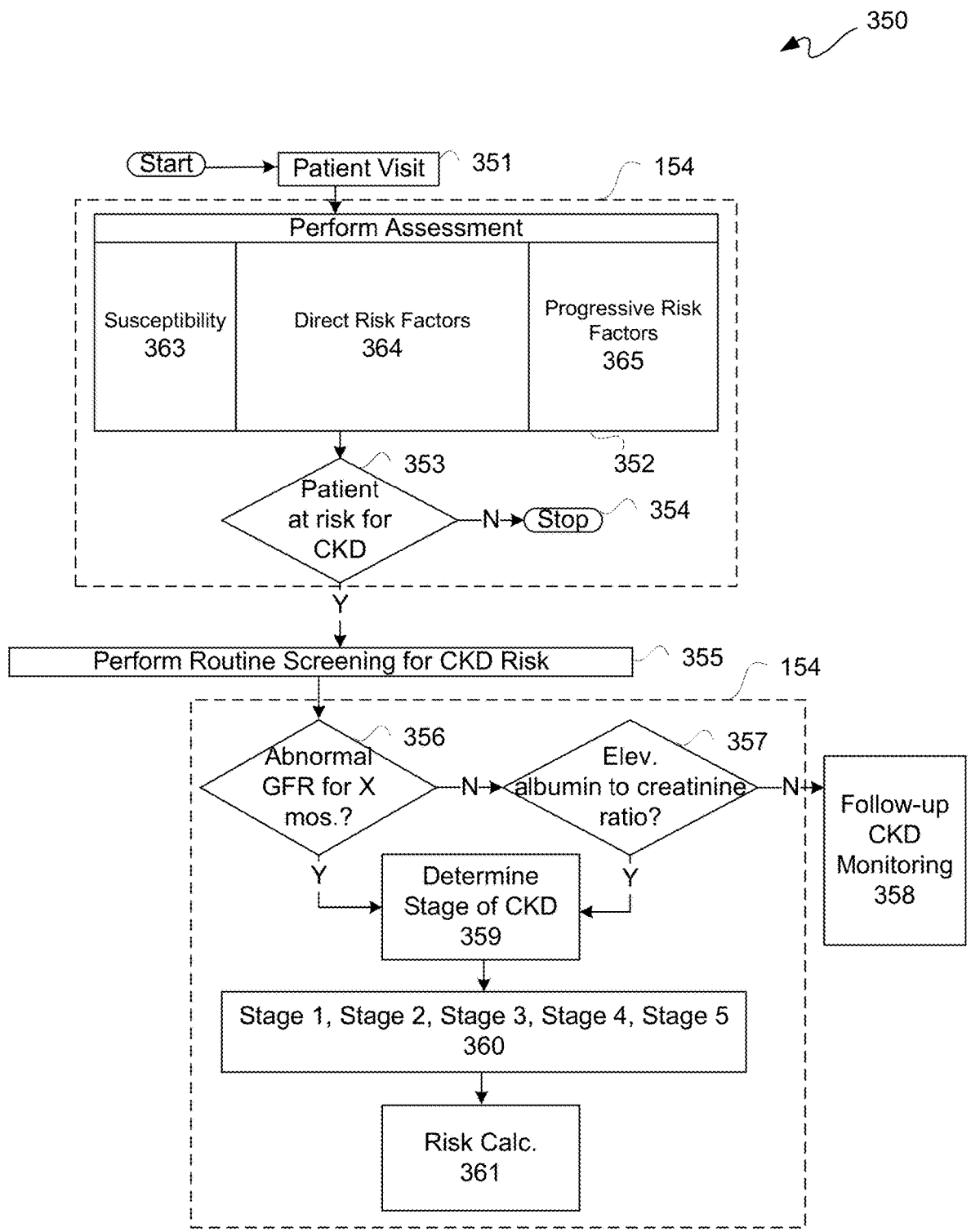
FIG. 13 is a flow diagram depicting an exemplary chronic kidney disease ("CKD") assessment flow which may be used in the PCH care delivery system of FIG. 8.

AI-PCDSS app 154 via treatment delivery flow 330 for a PCH care delivery system 190 interrogates patient data to determine whether a patient is suffering from a potential kidney failure. Along those lines, FIG. 13 is a flow diagram depicting an exemplary CKD assessment flow 350 which may be used in a PCH care delivery system 190. More particularly, AI-PCDSS app 154 may be configured to perform a subset of operation of CKD assessment flow 350 as designated with dashed boxes labeled as AI-PCDSS app 154.

If a patient's vital statistics and/or answers to questionnaires indicate an early stage of kidney disease from a patient visit at operation 351, such CKD assessment flow 350 may proceed at operation 352 by AI-PCDSS app 154. AI-PCDSS app 154 may perform an assessment on a patient's susceptibility 363. Susceptibility may be determined in part by for example an age greater than or equal to 60 years, a family history of CKD, and/or racial status or ethnicity. PCDSS app 154 may perform an assessment on a patient's direct risk factors 364 and progressive risk factors 365 as part of such assessment at operation 352. Direct risk factors may include one or more of diabetes, hypertension, autoimmune disease(s), lower urine tract obstruction, metabolic syndrome, systemic infections, urinary tract infections, urinary stones, drug toxicity, and/or exposure to nephrotoxic drugs. Progressive risk factors may include one or more of high levels of proteinurla, malignant hypertension, poor glycemic control, smoking hperlipidemia, and/or drug use.

At operation 352, during a patient's clinic visit at operation 351 or through such health questionnaire inputs/history discussed in operation 331 of FIG. 12 data may be obtained by PCDSS app 154 for determining a patient's risk for CKD. Such medical and other data collected and obtained by PCDSS app 154 may be used at operation 353 to determine by PCDSS app 154 if such patient is at risk for CKD at operation 353. If a patient is determined at operation 353 by PCDSS app 154 to not be at risk for CKD, CKD assessment flow 350 may stop at 354. If such patient is determined at operation 353 by PCDSS app 154 to be at risk for CKD, then routine screening may be ordered by PCDSS app 154 and performed at operation 355 to determine an estimated Glomerular Filtration (GFR) from a Microalbumin test urinalysis for presence of white and red blood cells. Such a screening may use a serum crepane to determine an estimated GFR from a Microalbumin test result. Such screening may further obtain data for a patient's albumin to creatinine ratio.

At operation 356, PCDSS app 154 interrogates test results from screening at operation 355, as well as prior screening operations, to determine if a patient has an abnormal GFR in more than three (3) months. If PCDSS app 154 determines at operation 356 that a patient does not have an abnormal GFR in more than three (3) months, then at operation 357 PCDSS app 154 determines whether such patient has an elevated albumin to creatinine ratio from test results of operation 355. For diabetic patients with a greater than 30 mg albumin/1 g creatinine ratio and for non-diabetic patients with a greater than 300 mg albumin/creatinine ratio, a follow-up CKD monitoring may be ordered by AI-PCDSS app 154 for follow-up at operation 358. Operation 358 may be to periodically test patients at risk for CKD and/or periodically counsel patients at risk for CKD but found not to have CKD to reduce risk factor when possible. This testing and/or counseling generally may be performed annually or bi-annually. However, by use of smart patch 650, patient monitoring on hemoglobin levels may be throughout a year in order to preempt known indicators of anemia as a CKD complication.

If at operation 356 or 357 a patient test positive for having an abnormal GFR as indicated above or an elevated albumin/creatinine ratio as indicated above, then at operation 359 a stage of CKE may be determined by AI-PCDSS app 154. Operation 359 may include operations 360 and 361 in order to make such determination.

At operation 360, AI-PCDSS app 154 determines a CKD stage from 1 to 5 based on a GFR found at operation 355 or based on statistical analysis of a history of GFRs, such as a three-month history for example. Such a statistical analysis may simply be an average or may be a trending average for example. CKD stages 1 to 5 respectively are for GFR: greater than 90, from 60 to 89 inclusive, from 30 to 59 inclusive, from 15 to 29 inclusive, and less than 15. Such stages may be adjusted based on a risk calculation of operation 361, where AI-PCDSS app 154 may be configured with a risk calculator to adjust stages based on a patient's age, sex, protein ACR, and GFR in this example. For example, 1 in 3 Americans over age 20 are at risk for kidney disease due to: high blood pressure, a family history of kidney failure, being age 60 or over. Additional risk factors are obesity or being a member of minority groups including African-Americans, Hispanics, Asians, Pacific Islanders, and Native American.

Figure 14:
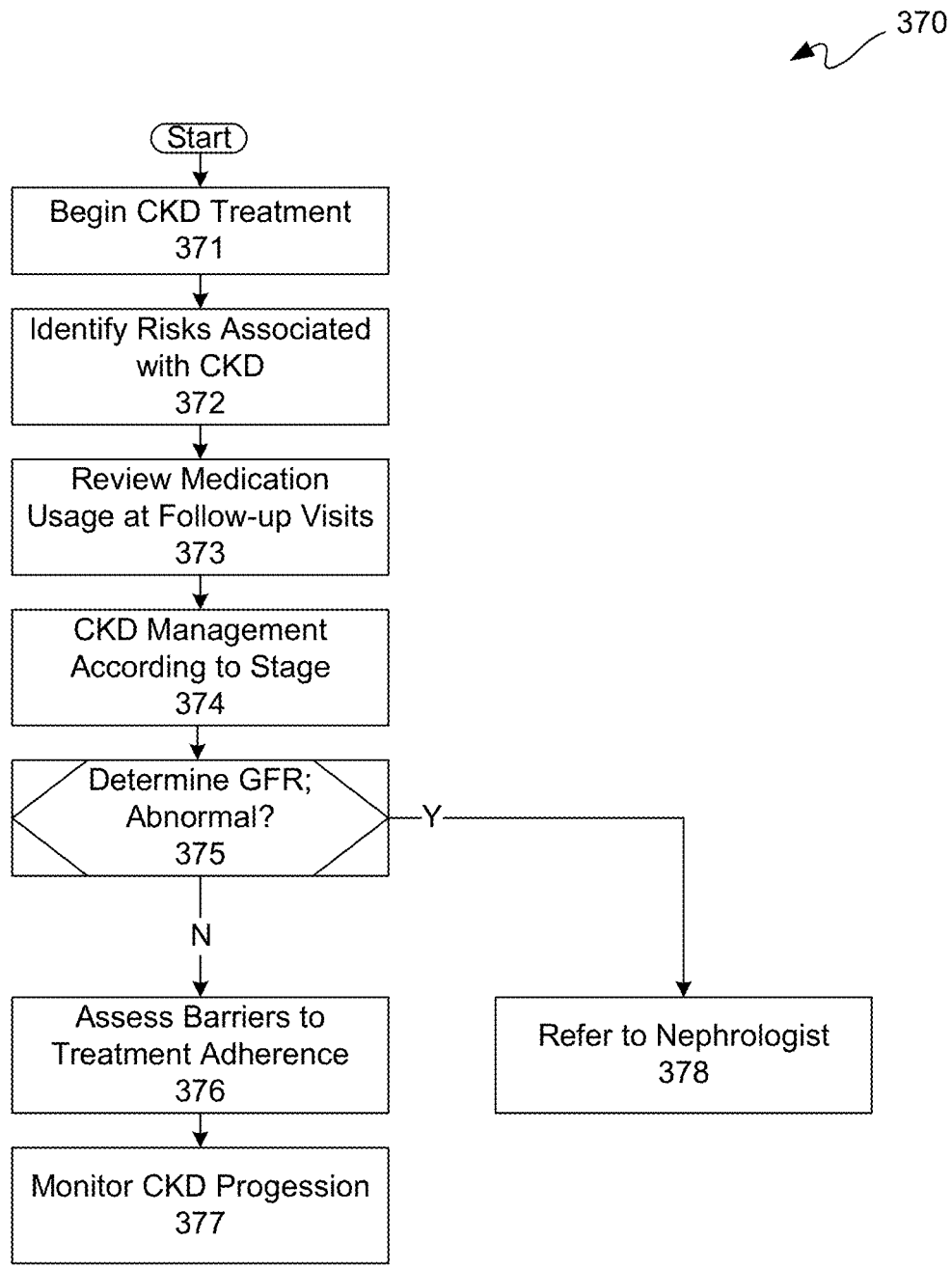
FIG. 14 is a flow diagram depicting an exemplary clinical action plan flow which may be used in the PCH care delivery system of FIG. 8.

FIG. 14 is a flow diagram depicting an exemplary clinical action plan flow 370 which may be used in a PCH care delivery system 190. AI-PCDSS app 154 may be configured to be supervised by or collaborate with a nephrologist, as described below in additional detail.

At operation 371, CKD treatment may begin by developing a clinical action plan. AI-PCDSS app 154 may suggest or collaborate with a nephrologist and/or a Primary Care Provider (PCP) to develop a clinical action plan. Some clinical action plan activities a PCP may supervise AI-PCDSS app 154, others a nephrologist may supervise AI-PCDSS app 154; and still others a PCP and a nephrologist may co-manage supervision of AI-PCDSS app 154. Such a clinical action plan may provide one or more of the following: evaluation of the type of kidney disease; evaluation and management regime for comorbid conditions or conations (all CKD stages); slow such loss of kidney function (all CKD stages); prevent and treat cardiovascular disease (all CKD stages); prevent and treat complications of deceased kidney function (all CKD stages); prepare for kidney failure and replacement therapy (CKD stage 4); and replace kidney function (CKD stage 5).

At operation 372, risks associated with CKD may be identified by AI-PCDSS app 154 to aid a physician. AI-PCDSS app 154 may identify the type of kidney disease and complications of kidney disease such as anemia, hypertension, malnutrition, bone diseases, metabolic acidosis, congestive heart failure, hyperkalemia, edema determined to be fluid overload, and/or neuropathy. AI-PCDSS app 154 may evaluate risk of loss of kidney function, evaluate comorbid condition, and evaluate risk for cardiovascular disease. Along those lines, AI-PCDSS app 154 may further be configured for processing heart monitoring data, as previously described.

AI-PCDSS app 154 may review medication usage at operation 373. At follow-up patient visits, AI-PCDSS app 154 may evaluate for dose adjustments based on level of kidney function, evaluate for adverse effects of medications of kidney functions (NSAID, IV contrast), evaluate for drug interactions, counsel patients to avoid nephrotoxic drugs and IV contrast, evaluate appropriateness for ARB/ACE inhibitor with diagnosis of hypertension, and evaluate need for therapeutic drug monitoring.

At operation 374, CKD management may be based according to a diagnosed stage of CKD by AI-PCDSS app 154. At operation 375, a screening operation may be performed to obtain results or results from a prior screening operation, such as previously described with reference to operation 355, may be used to determine whether a patient has an abnormal GFR for a period greater than 3 months.

If it is determined at operation 375 that a GFR is normal, then barriers to treatment adherence may be assessed at operation 376 by a medical professional. Examples of barriers to treatment adherence may include one or more of lack of family and social support, depression, stress, poor coping mechanisms, and limited access to medications and care, among others. At operation 377, after an assessment at operation 376, a medical professional may direct a patient to undergo monitoring of CKD progression.

If it is determined at operation 375 that a GFR is abnormal, then a referral to a nephrologist may be made at operation 378. Such a referral may be informed by guidelines to observe in referring to a nephrologist for different CKD stages. For example, a consultation to a nephrologist at CKD stage 1 is encouraged if hematuria or significant proteinuria is present. A consultation to a nephrologist at CKD stage 2 is encouraged if GFR declines. A consultation to a nephrologist for GFR being less than 4 ml/mm/yr, at stage 3 is generally made for all patients with CKD, and patients are typically referred to nephrologist for evaluation when GFR is lower than 30 ml/min/1.73.

Figures 1, 15:
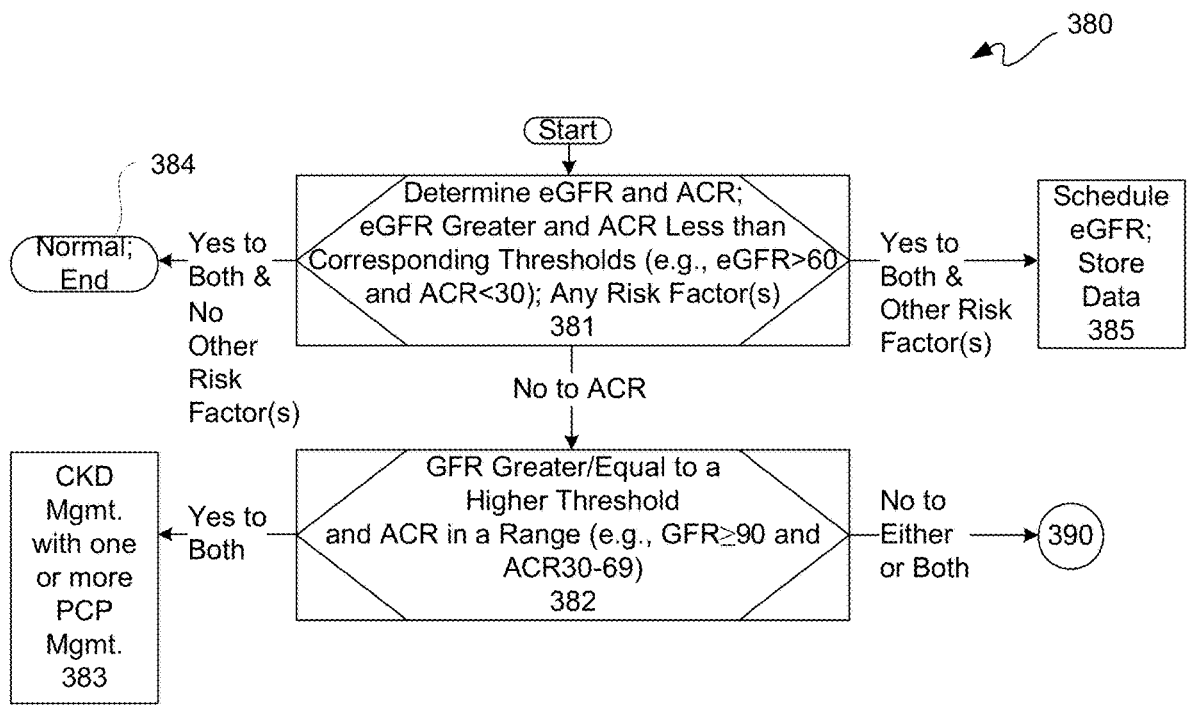
Figures 2, 15:
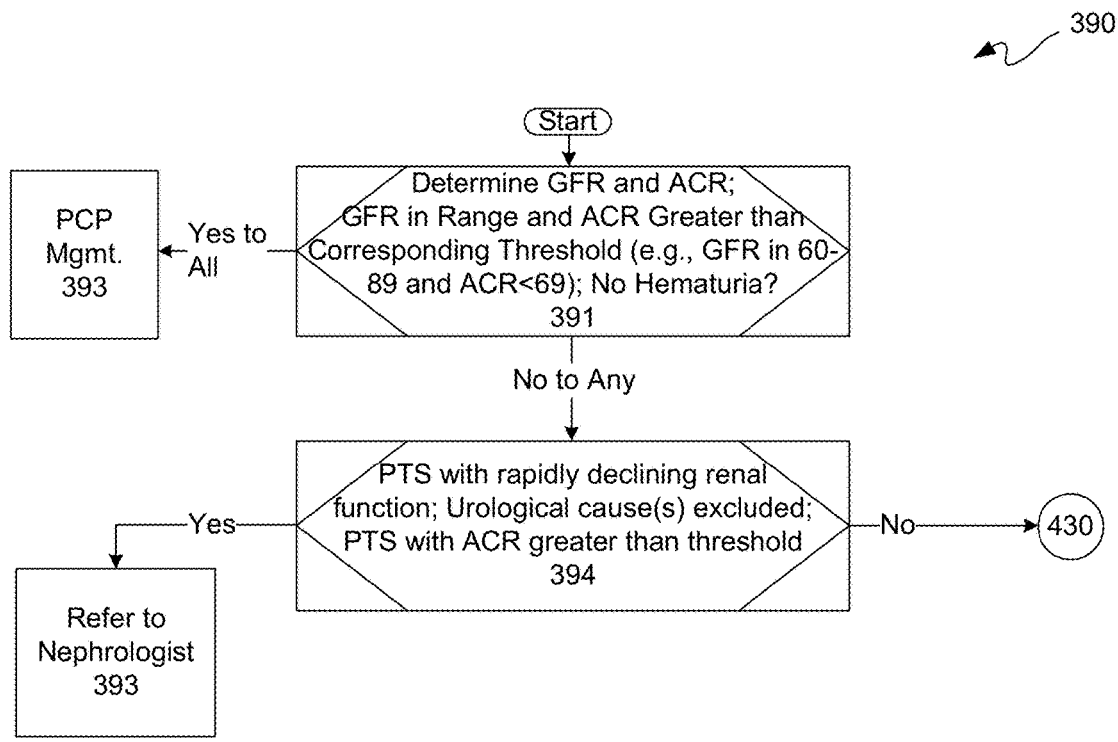
Figures 3, 15:
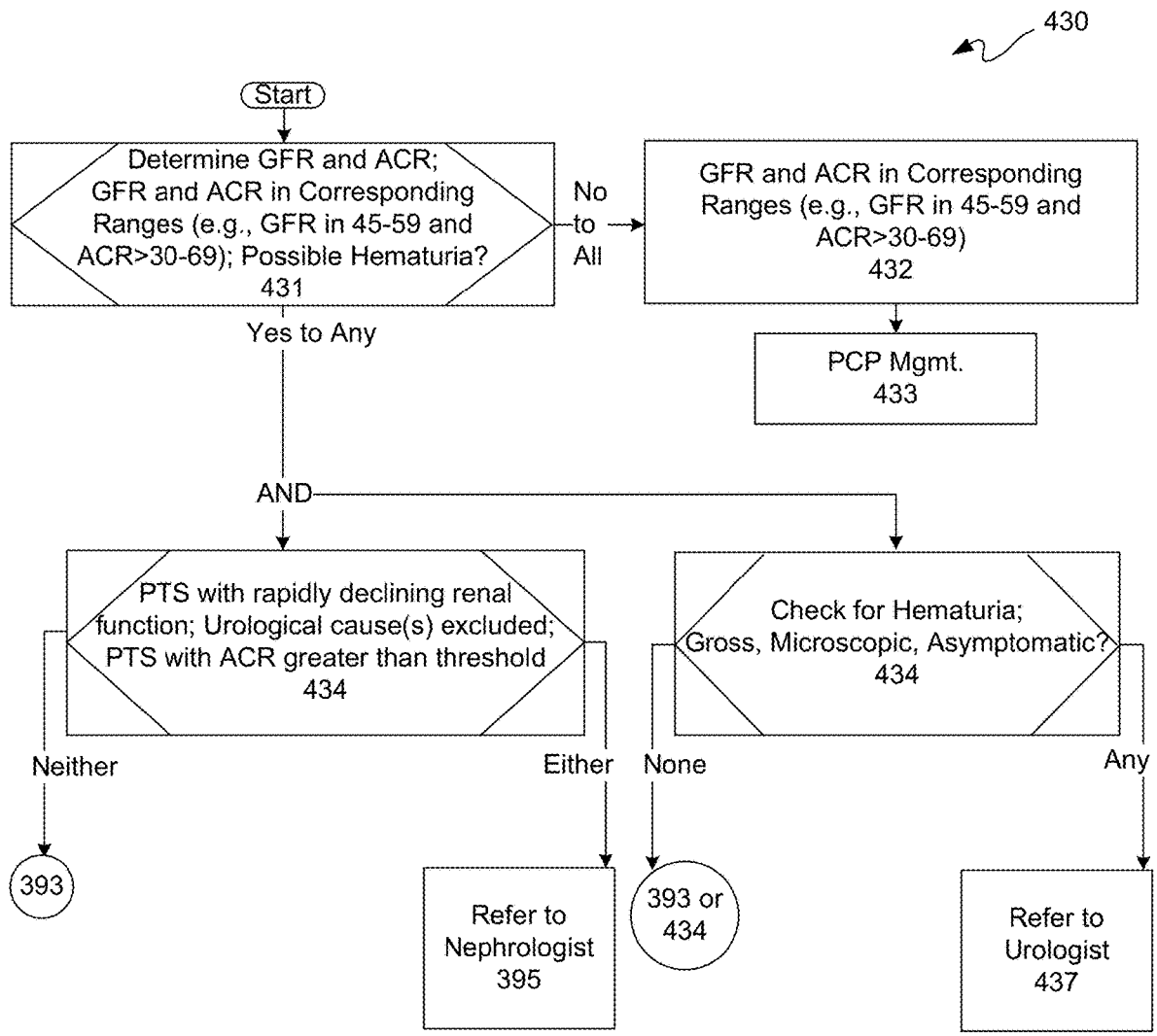
Figures 4, 15:
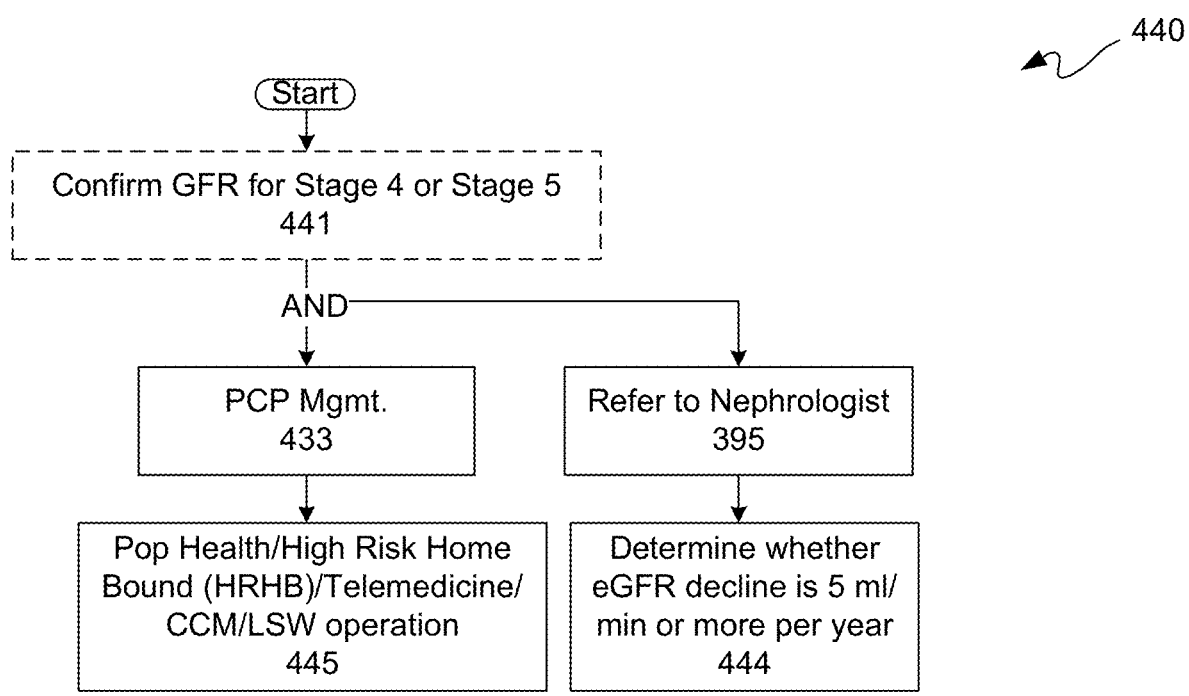

FIG. 15-1 is a flow diagram depicting an example of a CKD management flow 380 for CKD stages 1 and 2. FIG. 15-2 is a flow diagram depicting an example of a CKD management flow 390 for a CKD stage 3A. FIG. 15-3 is a flow diagram depicting an example of a CKD management flow 430 for a CKD stage 3B. FIG. 15-4 is a flow diagram depicting an example of a CKD management flow 440 for CKD stages 4 and 5. Flows of FIGS. 15-1 through 15-4 may be used for a CKD management operation 374 of FIG. 14, and such flows are further described with simultaneous reference to FIGS. 1 through 15-4. Furthermore, such CKD management flows may depend upon a diagnosis at operation 360 of a CKD stage, as previously described. Along those lines, AI-PCDSS app 154 may direct a physician to an appropriate CKD management path, as described below in additional detail, where such physician may supervise AI-PCDSS app 154. Unless otherwise indicated by context, such as a test to be performed or a physician to take action, operations of flows of FIGS. 15-1 through 15-4 may be under control of or lead by AI-PCDSS app 154.

With particular reference to FIG. 15-1, eGFR and ACR for CKD management are determined for management of CKD stages 1 and 2. If at operation 381 it is determined that a patient has an eGFR greater than 60 ml/min and ACR lower than 30, and no other risk factor for CKD are present, such status may be considered as normal and CKD management flow 380 may end at operation 384. If at operation 381 it is determined that a patient has an eGFR greater than 60 ml/min and ACR lower than 30, but a risk factor is present for CKD, an eGFR may be scheduled at 385, which may be repeated each 12 months. Such eGFR and ACR data may be stored at 385 for access by AI-PCDSS app 154 for scheduling such maintenance.

If at operation 381 it is determined that a patient has an eGFR greater than 60 and ACR greater than or equal to 30, then at operation 382 it may be determined if a patient has a GFR greater than or equal to 90 ml/min and an ACR in a range of 30-69 inclusive. If such thresholds at operation 382 are both met, then operation 383 may be performed, namely CKD management with one or more of PCP management, in-clinic, in-home management, telemedicine management, or chronic care management (CCM). Management at operation 383 may include one or more of: blood pressure control management (e.g., aiming for 140/90 mmHg or better) which may include use of angiotensin converting enzyme inhibitors (ACE-Is) or angiotensin receptor blockers (ARBs); reduction of cardiovascular (CV) disease risk; identification of progressive CKD; monitoring and evaluating album inuria and hematuria (e.g., annually with an office-based lab (OBL) or other lab); renal ultrasound (e.g., annually), lifestyle advice; medication review (e.g., avoidance of nephrotoxic medications); immunizations; potassium monitoring; bone condition monitoring; diabetes management; or anemia management with a CKD smart patch 650 driven by AI-PCDSS app 154.

However, if such thresholds at operation 382 are not both met, such as either or both a GFR below 90 ml/min or an ACR not in a 30 to 69 range inclusive, then CKD management flow 380 may be transitioned to CKD management flow 390. Along those lines, at operation 391 for CKD management in stage 3A it may be determined whether a patient has a with GFR in a range of 60 to 89 ml/min inclusive, an ACR greater than 69, and no hematuria.

If a patient's GFR is determined at operation 391 to be in a 60 to 89 ml/min inclusive range with ACR lower than or equal to 69 with no hematuria, then PCP management may proceed at operation 393. PCP management may to include one or more of: blood pressure control management (e.g., aiming for 140/90 mmHg or better) which may include use of angiotensin converting enzyme inhibitors (ACE-Is) or angiotensin receptor blockers (ARBs); reduction of cardiovascular (CV) disease risk; identification of progressive CKD; evaluating album inuria and hematuria (e.g., annually with an office-based lab (OBL) or other lab); renal ultrasound (e.g., annually), lifestyle advice; medication review (e.g., avoidance of nephrotoxic medications); immunizations; potassium monitoring; bone condition monitoring; diabetes management; or anemia management with a CKD smart patch 650 driven by AI-PCDSS app 154.

If, however, at operation 391 a patient's GFR is determined to be below 60 ml/min, or has an ACR greater than 69, or possibly has some type of hematuria (i.e., blood in urine), then a determination using a proteinuria/hematuria or other screening test ("PTS") may be made at operation 394. Excessive protein excretion in urine is a significant risk factor for both renal disease and for cardiovascular morbidity and mortality. Unlike haematuria or hematuria, proteinuria is generally renal in origin. Management of patients with proteinuria may include: quantification by albumin/creatinine or protein/creatinine ratio (ACR or PCR) determination; a test for hematuria (e.g., a urine dipstick test); measurement of serum creatinine; and blood pressure measurement.

At operation 394 it may be determined whether PTS with rapidly declining renal function is present by a declining GFR of more than 5 ml/min per year. Additionally, any and all urological causes may be determined to be excluded as a cause for such declination. Or, it may be determined that a PTS with ACR 300 mg/g greater than 30 mg/mmol is present. If any of these conditions at operation 394 is true and any and all urological disorders are ruled out, then referral to a nephrologist at operation 395 may be initiated by AI-PCDSS app 154. If, however, none of these conditions at operation 394 is true or a urological disorder may be present, then a transitioning to CKD stage 3B management flow 430 may be performed.

With particular reference to FIG. 15-3, CKD stage 3B management flow 430 may begin with a GFR and ACR check at operation 431. If at operation 431 it is determined that a patient's GFR is in a range of 59 ml/min or less, such as in a range of 45 to 59 ml/min inclusive for CKD stage 3B, with an ACR greater than 69, such as in a range of 30 to 69 inclusive for CKD stage 3B, with a possible hematuria, then operations 434 and 435 may be performed for multi-disciplinary coverage. Operation 434 is as previously described for operation 394, except urological cause is not excluded in this operation but rather possibly in operation 435, and a referral to a nephrologist at operation 395 is preformed if either condition of operation 434 is met. If neither condition of operation 434 is met, then PCP management may be performed at operation 393.

Operations 434 and 435 may be performed in parallel or in series, the latter with operation 435 preceding operation 434 so as to rule out or rule in a hematuria condition affecting kidney function. For operation 434 in parallel or series with operation 435, at operation 435 tests may be run for presence of a hematuria. Along those lines, test may be run for a gross hematuria, a microscopic hematuria associated with lower urinary tract symptoms, and an asymptomatic invisible hematuria. If any of these hematuria conditions are found to be present as determined at operation 435, then a referral to a urologist may be made at operation 437. If hematuria is ruled out at operation 435, then if not performed in parallel with operation 434 such operation 434 may be performed. If, however, operations 434 and 435 are performed in parallel and hematuria is ruled out at operation 435, then PCP management may be performed at operation 393.

If a hematuria condition is not present or has been previously ruled out, then at operation 431 it may be determined whether a patient shows a GFR rate in a range CKD stage 3B range of 45 to 49 ml/min inclusive with ACR greater than 69, namely beyond an ACR in a 30 to 69 inclusive range as previously described, then PCP management may be performed at operation 433. PCP management at operations 433 and 393 are the same, except PCP management at operation 433 includes a referral to a nephrologist as there is no urological disorder causing loss of kidney function for such stage 3B GFR and ACR data.

For a stage 4 or 5 diagnosis, at optional operation 441 of CKD management flow 440 of FIG. 15-4 a confirmation of such diagnosis may be performed. For stage 4 CKD, a GFR in a range of 15 to 29 ml/min inclusive may be used, and for a stage 5 CKD, a GFR in a range of less than 15 ml/min may be used. If there is no confirmation, but rather a GFR indicates a lower stage of CKD, then management for such lower stage CKD may be used as previously described herein.

Both stages 4 and 5 may proceed directly to PCP management 393, as previously described, and to a referral to a nephrologist at operation 395 to manage CKD progression. From operation 393 of CKD management flow 440, a Pop Health/High Risk Home Bound (HRHB)/Telemedicine/CCM/LSW operation 445 may be performed in order to manage co-morbidities. Further at operation 445, a patient can be enrolled to specific Pop Health Programs to reduce disease risks, and a patient may use telemedicine for periodic assessment and monitoring of conditions. Additionally, at operation 445, eGFR may be monitored based on frequency of testing guidelines, and a patient may undergo a renal ultrasound. Further at operation 445, a patient's anemia may be managed with a CKD smart patch 650 driven by AI-PCDSS app 154. Other operations that may be performed at operation 445 may include a Collaborative Care Management (CCM)/end stage renal disease (ESRD) service and a phycologist (Psy)/licensed Clinical Social Worker (LCSW) for behavioral health integration (BHI).

After a patient is to be referred to a nephrologist to manage CKD progression at operation 395, at operation 444 it may be further determined whether an eGFR decline is 5 ml/min or more per year. Any such new finding of such a reduced GFR may be repeated within two weeks to rule out an acute kidney injury (AKI). Furthermore, at operation 444 to identify progression of GFR decline, an eGFR may be taken thrice within ninety 90 days. Additionally, at operation 444, a patient may be prepared for kidney failure and replacement therapy, and a patient's kidney function may be replaced, such as with dialysis or transplant.

Figure 16:
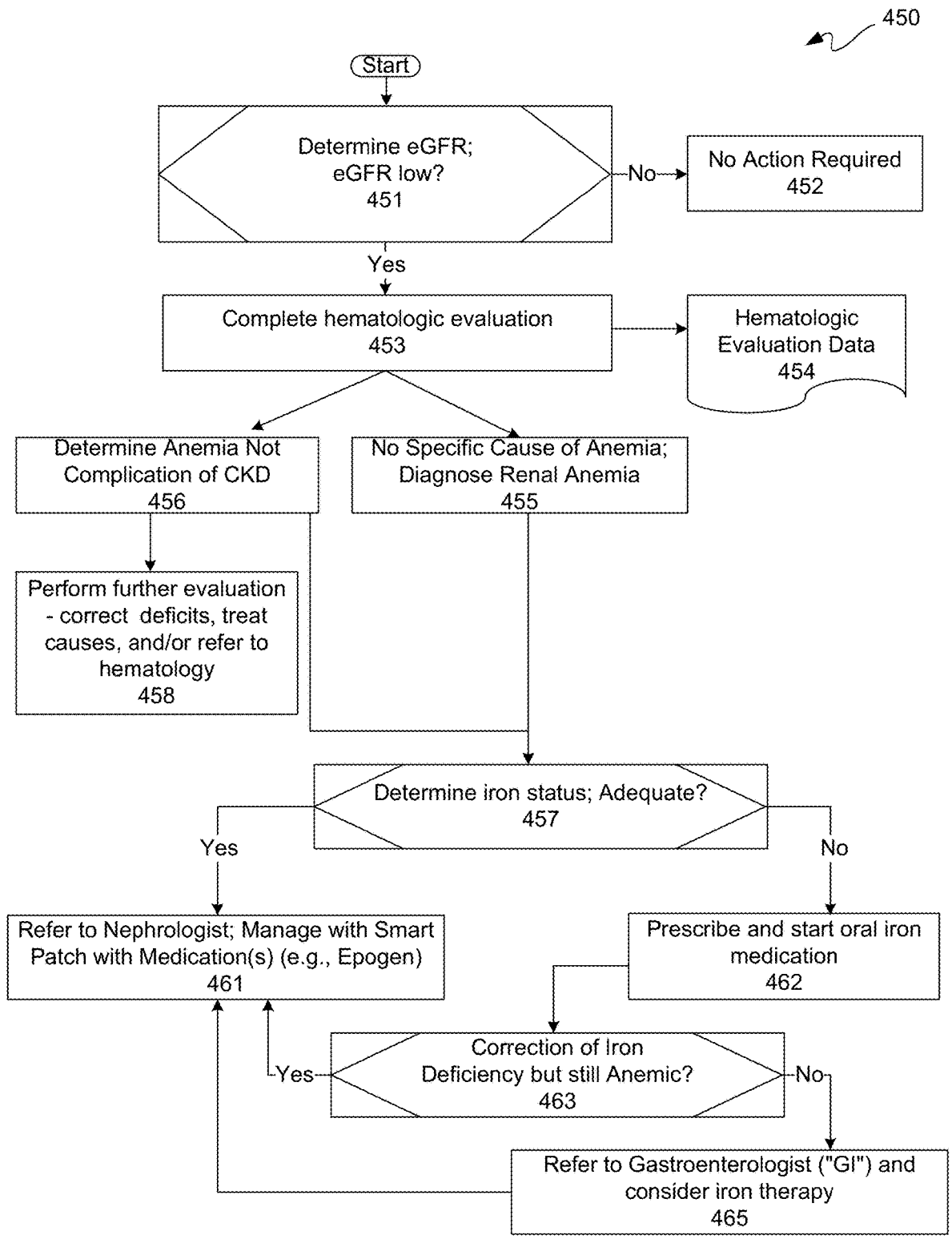
FIG. 16 is a flow diagram depicting an example of an anemia flow indicative of a CKD complication following an assessment.

FIG. 16 is a flow diagram depicting an example of an anemia flow 450 indicative of a CKD complication following an assessment. At operation 451, an assessment may begin when a CKD patient has an eGFR, and such eGFR is determined to be too low or within normal limits. A patient with an eGFR lower than 60 ml/min and with a hemoglobin count lower than 13 g/dl for a male patient or hemoglobin count lower than 12 g/dl for a female patient may be deemed too low. If such hemoglobin counts are not found to be apparent based on a corresponding test therefor, then no action may be taken at operation 452.

However, if such hemoglobin counts are found to be positive or too low, then a complete hematologic evaluation may be performed at operation 453. Data 454 from operation 453 may include one or more of: a complete blood cell count; red blood cell indices; a reticulocyte count; iron measurements such as serum iron, total iron-binding capacity, percent transferrin saturation and serum ferritin; and data from a stool for occult blood.

If anemia is not a complication of CKD as determined at operation 456 such as a result of data 454 processed by AI-PCDSS app 154, then a further evaluation of anemia may be made at operation 458. At operation 458, operations to correct such deficits, treat such causes, and/or refer to hematology (if necessary) may be performed. Furthermore, if no specific causes of anemia can be determined at operation 455 from data 454 processed by AI-PCDSS app 154, then AI-PCDSS app 154 may diagnose a patient with renal anemia at operation 455.

From either of operations 455 or 456, a patient's iron status may be determined at operation 457. From operation 456, both of operations 458 and 457 may be subsequently performed as part of a multi-disciplinary evaluation. If such patient's iron status is determined at operation 457 to be adequate, then at operation 461 such patient may be referred to a nephrologist to evaluate anemia management with a smart patch 650 with Epogen in a drug reservoir thereof controlled by AI-PCDSS app 154. Such anemia may be managed with Epogen if a hemoglobin (Hb) level is equal to or lower than 10 g/dl. When, however such patient is iron deficient as determined at operation 457, then at operation 462 an oral iron medication may be prescribed and started.

At operation 463 it may be determined that such iron deficiency is corrected by that a patient is still anemic, such as with a hemoglobin count of lower than 10 g/dl. If despite such iron deficiency correction such patient still suffers from anemia, then operation 461 may be performed. However, if a patient still has an iron deficiency three months from starting oral iron medication at operation 462, then at operation 465 such patient may be referred to a gastroenterologist and consider an iron therapy IV or smart patch 650 with an iron medication in a drug reservoir thereof controlled by AI-PCDSS app 154. After operation 465, a patient may be referred to a nephrologist at operation 461.

Figure 17:
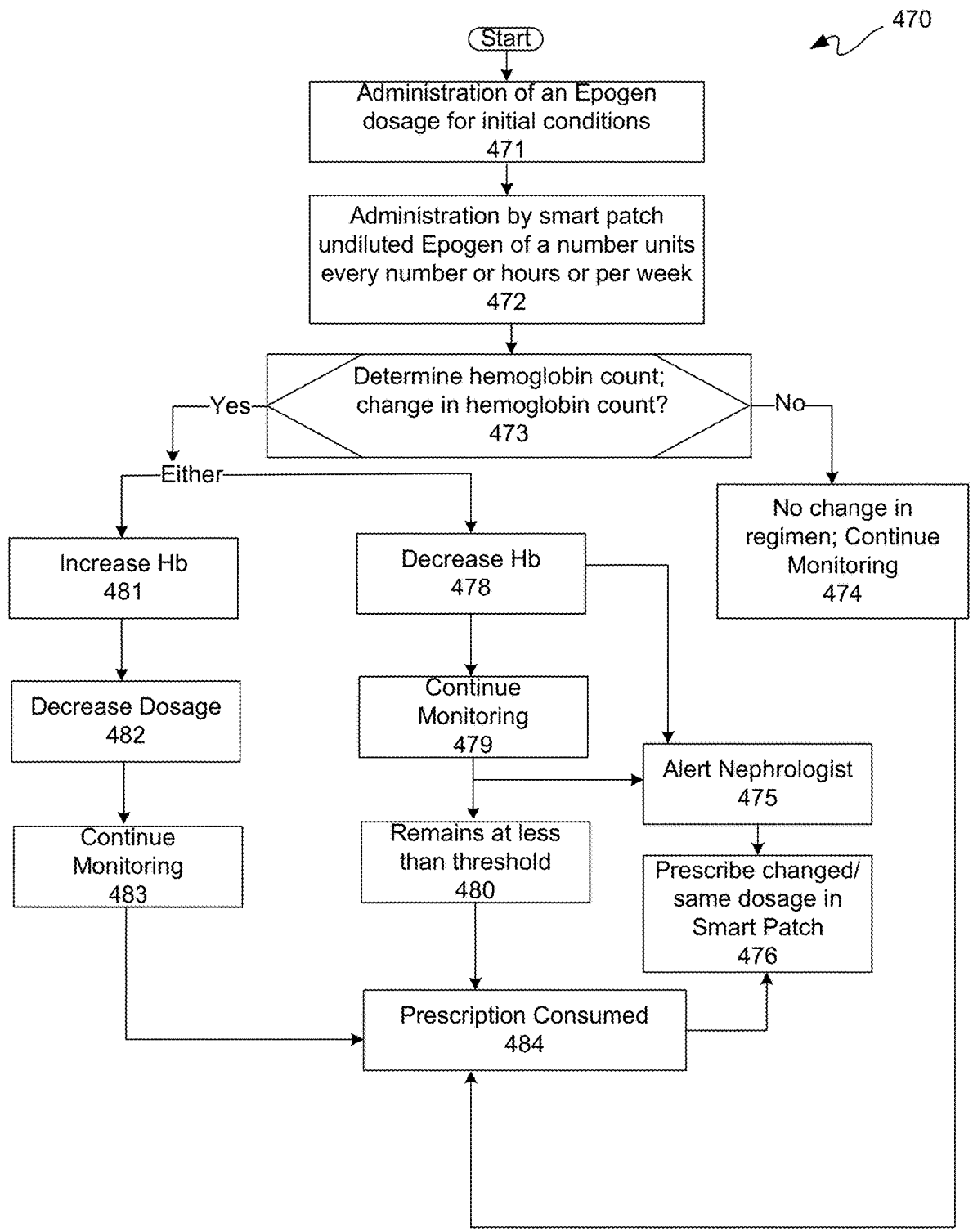
FIG. 17 is a flow diagram depicting an example of an Epogen dosage flow.

FIG. 17 is a flow diagram depicting an example of an Epogen dosage flow 470. The following example includes particular values for a particular diagnosis and condition of a patient for purposes of clarity by way of example and not limitation. Accordingly, these and/or other values may be used in treating anemia.

Epogen dosage flow 470 may be configured in AI-PCDSS app 154 and smart patch 650. More particularly, Epogen dosage flow 470 in this example is for a condition of an anemic CKD patient in an Erythropoiesis-stimulating agents (ESA) therapy with a hemoglobin count that is equal to 10 g/dl; sufficient to call for an administration of an Epogen dosage at initial conditions 471.

A smart patch 650 with Epogen may be configure to release undiluted Epogen of 50 units every 48 hours or 160 units per week to be given to a patient at operation 472. In a 30-day prescription period at operation 472 may be coupled with a hemoglobin count daily monitoring using sensor 205.

At operation 473, to take into consideration hemoglobin count changes that may take place in two (2) weeks at a time, an archive of hemoglobin counts, such as stored in memory 675, as sensed, such as by sensor 205, may be accessed by AI-PCDSS app 154, and a check for such changes in hemoglobin count may be made. Further at operation 473, a determination may be made by AI-PCDSS app 154 as to whether a change in hemoglobin count has occurred or not.

If a change in such hemoglobin count has occurred in a couple of weeks and such increase of such hemoglobin count goes up by 1 g/dl as determined at operation 481, an Epogen dose may be decreased by 26% at operation 482. From operation 482, at operation 483 such hemoglobin count monitoring may be continued for another two weeks, and so on until a 30-day prescription is completely consumed as determined at operation 484.

From operation 484, at operation 476 a nephrologist can prescribe another smart patch 650 configured with Epogen for a patient when as applicable. Such smart patch 650 may be configured with a new dosage programmed into a microcontroller of a medication delivery system for another 30-day prescription period.

Similarly, if at operation 473 a hemoglobin count taking place in 2 weeks, results in a decrease in such hemoglobin count by 1 g/dl as determined at operation 478, then such hemoglobin monitoring may be continued for another two weeks at operation 479. At operation 475, from operation 478 and/or 479 a nephrologist may be alerted of such result through one or more IoT devices, such as a smartphone, an electronic health record device, or a telemedicine application. This information may be provided to operation 476 for consideration in a prescription.

At operation 480 from operation 479, it may be determined whether a patient's hemoglobin level remains at less than 10 g/dl. Again, such monitoring of hemoglobin count may continue until a 30 day prescription is fully consumed as determined at operation 484. Operation 476, as previously described, may be used to follow upon a referral to such nephrologist for another smart patch 650 to be given for another round of 30-day prescription with a new Epogen dosage programmed into a medication delivery system thereof.

If, however, at operation 473 it is determined that there are no changes in two weeks of monitoring upon a patient's hemoglobin count as staying at 10 g/dl, then no changes in such regimen may be made as determined at operation 474 such as by AI-PCDSS app 154. AI-PCDSS app 154 may continue such hemoglobin count monitoring for another two weeks at operation 474 until a 30-day prescription is ended as determined at operation 484. Thereafter, operation 476, as previously described, may be repeated. A nephrologist may find it necessary to have Epogen be further given to an anemic patient with CKD on a basis of previously identified for hemoglobin level in operation 471. However, at operation 476 such dosage may be further calculated and programmed into a medication delivery system of a smart patch 650.

Epogen dosage flow 470 in combination with a previously described diagnostic system through a smart medication patch to ascertain a patient's hemoglobin count which determines a formulation and prescription of Epogen or its biosimilars for patients under medication compliance. This facilitates patients receiving an immediate treatment through the efficiency of a smart medication patch drug delivery system. Moreover, such a controlled dosage may reduce or negate health complications resulting from inaccurate Epogen dosing and/or prescriptions.

As described hereinabove, a PCH care delivery system 190 having a PCDSS 100 may have an AI-PCDSS app 154. AI-PCDSS app 154 may be stored in various locations for a client portion and backend portion; however, examples of application programs 1048 and 1135 may be used. Along those lines, a chat bot client and a client app 1118 and 1119 may be stored in apps 1135, and a touch screen client interface 1117 may be stored in storage 1129 of a mobile device 1120, such as in FIG. 11 for example. However, in another example, RTM device 130 may store a client app 1119. However, these or other client electronic devices described herein may be used for communication between a Cloud-enabled server based AI-PCDSS app 154B and a smart patch 650.

PCH care delivery system 190 may provide data capture, monitoring and near real-time diagnosis capabilities powered by a Cloud-enabled server based AI-PCDSS app 154. Along those lines, PCH care delivery system 190 can detect, analyze and quantify hemoglobin count to preempt known indicators of anemia, such as hemoglobin levels and monitoring inputs. PCH care delivery system 190 can provide a physician legitimate groundworks for a less complicated interpretation of electronically acquired and retrieved health data to further medication dosing and/or dispensing, such as to the extent of modifying the amount of Epogen or biosimilars being delivered to remotely located clinical patients for example.

AI-PCDSS app 154 in stages may constitute a portion of a tripartite telemonitoring approach, alongside PHCDS and PCDSS supporting early detection and monitoring of CKD. Additionally, to further presume the above-mentioned diagnosis and treatment, AI-PCDSS app 154 may learn through data from the individual patient. Moreover, an individual physician's knowledge may be supplemented by this learning, such as for a remote telemonitoring system, which at home diagnosis and treatment; home dialysis for example through the portability of a smart medication patch 650. Smart patch 650 may be useful to help underserved and rural populations, save from hospitalization costs, and reduce or minimize clinic visits by stabilizing medication compliance with the aid of a telehealth system.

A smart patch 650 is wearable medication drug delivery device having a microneedles array for the administration of drug therapy to a user with a sensor to monitor their hemoglobin count and level. Smart patch 650 may have a unitary housing of graphene coating material which encapsulates a compartmentalized drug reservoir and a hemoglobin monitoring sensor for hemoglobin level diagnostics.

In combination with AI-PCDSS app, a medical smart patch uses a predictive, closed-loop control of transdermal drug delivery system by integrating the real-time (global or local) in situ monitoring of hemoglobin concentration combined with AI as a sensing feedback loop to a PCDSS platform's microcontroller and provide real-time updates to a micropump delivery rate for effective CKD management. Such a diagnostic and drug delivery system may provide a resolution to promote medication compliance and adherence to patients under dialysis treatment with uncomplicated, accurate, and efficient monitoring of their condition via a smart medical patch 650 conjointly with physician-telemedicine support and PCHDS systems.

Furthermore, even though CKD and heart conditions are described above for monitoring and treatment, smart patch 650 may be used for treatment of other medical conditions involving periodic TD drug therapy, including for example drug addiction, obesity, among others.

While a foregoing describes exemplary apparatus(es) and/or method(s), other and further examples in accordance with a one or more aspects described herein may be devised without departing from a scope hereof, which may be determined by a claims that follow and equivalents thereof. Claims listing operations do not imply any order of operations. Trademarks are a property of their respective owners.

What is claimed is:

1. A system for remotely administering a medication, the system comprising:
   a drug delivery device having:
      at least one reservoir in fluid communication with a needle;
      at least one actuator to drive a fluid within a respective at least one reservoir to the needle;
      a microcontroller to control operation of the at least one actuator; and
      a communication interface; and
      a dosage control loop configured for communication with the microcontroller and a hemoglobin sensor;
   a client electronic device configured with a client app for communication via the communication interface of the drug delivery device; and
   a networked computing device configured with a backend app for communication with the client app;
   wherein the backend app configured with programming for the management of the chronic kidney disease responsive at least in part to vital sign data including the hemoglobin count sensed,
   wherein the communication interface is configured to download and upload information from and to the backend app for and from the microcontroller via the client app;
   wherein the drug delivery device is a wearable device configured to be powered by a portable power source;
   wherein the drug delivery device configured for automated adjustment of dosage responsive to hemoglobin count sensed by the hemoglobin sensor for transdermal administration of medication for management of chronic kidney disease,
   wherein the programming for the management of the chronic kidney disease comprises different algorithms for different stages of the chronic kidney disease.

2. A system in accordance with claim 1, wherein the programming includes a first algorithm for stages 1 and 2, a second algorithm for stage 3A, a third algorithm for stage 3B, and a fourth algorithm for stages 4 and 5.

3. A system in accordance with claim 2, wherein the programming is configured with artificial intelligence subject to medical professional supervision or collaboration.

4. A system in accordance with claim 3, wherein the programming is configured for treatment delivery for diagnosing and treating patients with anemia.

5. A method for remotely administering a medication, the method comprising:
   obtaining a drug delivery device having:
      at least one reservoir in fluid communication with a needle;
      at least one actuator to drive a fluid within a respective at least one reservoir to the needle;
      a microcontroller to control operation of the at least one actuator;
      a power source to power the microcontroller;
      a communication interface; and
      a dosage control loop configured for communication with the microcontroller and a hemoglobin sensor;
   automatically adjusting a dosage provided by the drug delivery device responsive to hemoglobin count sensed by the hemoglobin sensor for transdermal administration of medication for management of chronic kidney disease;
   communicating between a client electronic device with a client app with the drug delivery device via the communication interface thereof;
   communicating between a networked computing device with a backend app for and the client app; and
   managing the chronic kidney disease responsive at least in part to vital sign data including the hemoglobin count sensed by the drug delivery device via the backend app, wherein the backend app is configured with programming for the management of the chronic kidney disease;
   wherein the communication interface is configured to download and upload information from and to the backend app for and from the microcontroller via the client app, wherein the drug delivery device is a wearable device configured to be powered by a portable power source,
   wherein the programming for the management of the chronic kidney disease comprises different algorithms for different stages of the chronic kidney disease.

6. A method in accordance with claim 5, wherein the programming includes a first algorithm for stages 1 and 2, a second algorithm for stage 3A, a third algorithm for stage 3B, and a fourth algorithm for stages 4 and 5.

7. A method in accordance with claim 6, wherein the programming is configured with artificial intelligence subject to medical professional supervision or collaboration.

8. A method in accordance with claim 7, wherein the programming is configured for treatment delivery for diagnosing and treating patients with anemia.

* * * * *